US008685718B2

(12) United States Patent
Wisniewski et al.

(10) Patent No.: US 8,685,718 B2
(45) Date of Patent: Apr. 1, 2014

(54) MUCOSAL IMMUNIZATION TO PREVENT PRION INFECTION

(75) Inventors: Thomas Wisniewski, Staten Island, NY (US); Einar M. Sigurdsson, New York, NY (US); Jose Alejandro Chabalgoity, Montevideo Cp (UY); Fernando R. Goni, Montevideo Cp (UY); Blas Frangione, New York, NY (US)

(73) Assignee: New York University, New York, NY (US)

( * ) Notice: Subject to any disclaimer, the term of this patent is extended or adjusted under 35 U.S.C. 154(b) by 231 days.

(21) Appl. No.: 10/558,276

(22) PCT Filed: May 20, 2004

(86) PCT No.: PCT/US2004/016242
§ 371 (c)(1),
(2), (4) Date: Nov. 18, 2005

(87) PCT Pub. No.: WO2005/019412
PCT Pub. Date: Mar. 3, 2005

(65) Prior Publication Data
US 2007/0059807 A1    Mar. 15, 2007

Related U.S. Application Data

(60) Provisional application No. 60/472,262, filed on May 20, 2003.

(51) Int. Cl.
*G01N 33/68*    (2006.01)
(52) U.S. Cl.
USPC .................... 435/320.1; 435/91.1; 435/252.1; 435/69.1; 536/23.1
(58) Field of Classification Search
None
See application file for complete search history.

(56) References Cited

U.S. PATENT DOCUMENTS

| 5,733,760 | A  | * | 3/1998  | Lu et al. ........................ 435/477 |
| 5,843,446 | A  |   | 12/1998 | Ladd et al.                                |
| 6,019,982 | A  |   | 2/2000  | Clements et al.                            |
| 6,290,954 | B1 | * | 9/2001  | Prusiner et al. ............ 424/130.1     |
| 6,436,407 | B1 |   | 8/2002  | Clements et al.                            |
| 6,440,423 | B1 | * | 8/2002  | Clements et al. .......... 424/236.1       |
| 6,514,503 | B1 | * | 2/2003  | Gizurarson et al. ....... 424/278.1        |
| 6,585,975 | B1 | * | 7/2003  | Kleanthous et al. ....... 424/200.1        |
| 7,135,181 | B2 | * | 11/2006 | Jensen et al. ............... 424/185.1    |
| 2003/0219459 | A1 | * | 11/2003 | Bachmann et al. ......... 424/199.1     |
| 2006/0165722 | A1 |   | 7/2006  | De Magistris et al.                     |

FOREIGN PATENT DOCUMENTS

WO    WO 03/045128    6/2003

OTHER PUBLICATIONS

Sigurdsson et al. (American Journal of Pathology, 2002, vol. 161, p. 13-17).*
Sigurdsson et al. American Journal of Pathology, 2002, vol. 161, No. 1, pp. 13-17.*
Irani et al. Annual Reviews in Medicine, 2003, vol. 54, p. 305-319.*
Coulthart et al. Canadian Medical Association, 2001, vol. 165, p. 51-58.*
Georgieva, Experimental Pathology and Parasitology, 2002, p. 60-63.*
Benkirane et al. Journal of Biological Chemistry, 1993, vol. 268, p. 26279-26285, in IDS of Nov. 18, 2005.*
Chabalgoity et al. Vaccine, 2001, vol. 19, p. 460-469, in IDS of Nov. 18, 2005.*
Peretz et al. (Nature 2001, vol. 412, p. 739-743).*
Kaneko et al. (JMB, 2000, vol. 295, p. 997-1007).*
Kotloff (Infection and Immunity, 2002, vol. 70, p. 2016-2021).*
Sigurdsson et al. (American Journal of Immunology, 2002, vol. 161, p. 13-17).*
Williamson et al. (PNAS, 1996, vol. 93, p. 7279-7282).*
Grones (Biochemical and Biophysical Research Communications, 1995, vol. 206, p. 942-947).*
Krasemann et al. (Journal of Immunological Methods, 1996, vol. 199, p. 109-118).*
Jackson and Collinge, Mol Pathol. 2001;54:393-399.
Gajdusek and Zigas, N. Eng. J. Med., 1957;257:974-978.
Gajdusek and Zigas,Am. J. Med., 1959;26:442-469.
Prusiner et al., Prion Protein Biology, 1998;93:337-348.
Ghetti et al., Proc. Natl. Acad. Sci. USA, 1996;93:744-748.
Ghetti et al., Mol. Neurobiol., 1994;8:41-48.
Medori et al., N. Eng. J. Med., 1992;326:444-449.
Goldfarb et al., Science, 1992;258:806-808.
Collinge, Hum. Mol. Genet, 1997;6:1699-1705.
Collinge et al., Nature, 1996;383:685-690.
Collee and Bradley, Lancet, 1997;349:636-641.
Will et al., Lancet, 1997;347:921-925.
Griffith, Nature, 1967;215:1043-1044.
Horwich and Weismann, Cell, 1997;89:499-510.
Prusiner, Science, 1982;216:136-144.
Kretzschmar et al., Am. J. Pathol., 1986;122:1-5.
Pocchiari et al., J. Gen. Virol., 1987;68(Pt 1):219-223).
Caughey and Race, J. Neurochem., 1992;59:768-771.
Ladogana et al., J. Gen. Virol., 1992;73(Pt 3):661-665.

(Continued)

*Primary Examiner* — Agnieszka Boesen
(74) *Attorney, Agent, or Firm* — Troutman Sanders LLP

(57) ABSTRACT

Vaccines against prion disease eliciting a humoral immune response when administered mucosally are described. The vaccines comprise a prion protein, a prion protein fragment, or a non-amyloidogenic prion protein homolog and an adjuvant suitable for inducing a humoral immune response after mucosal administration. Suitable adjuvants include cholera toxin subunit B, heat-labile enterotoxin and aluminum hydroxide. Alternatively, the vaccine comprises a vector encoding a prion protein, fragment, or homolog in an attenuated *Salmonella* host. The vaccines can be used to prevent or treat prion disease in humans and other mammals.

15 Claims, 5 Drawing Sheets

(56) References Cited

OTHER PUBLICATIONS

Tagliavini et al., Science, 1997;276:1119-1122.
Soto et al., Lancet, 2000;355:192-197.
Priola et al., Science, 2000;287:1503-1506.
Aucouturier et al., Clin. Immunol, 2000;96:79-85.
Aucouturier et al., J. Clin. Invest., 2001;108:703-708.
Wisniewski et al.Curr. Neurosci Reports 2002;2:400-4.
Biochem. Soc. Transact 2002;30:574-578.
Sigurdsson et al., Am J Pathol 2002;161:13-17.
Sigurdsson et al., Neurosci Lett, 2003;336:185-187.
Steinberg, New Scientist, 2002; 16:22.
Munch et al., J. Neural Transm., 2002;109:1081-1087.
Schenk, Nat. Rev. Neurosci., 2002;3:824-828.
White et al., Adv. Exp. Med. Biol., 1991;303:207-210.
Lauterslager et al., Vaccine, 2003;21:1391-1399.
Foss et al., Animal Health Research Reviews, 2000;1:3-24.
Sethi et al., Lancet, 2002;360:229-230.
Mannino and Gould-Fogerite, Pharm. Biotechnol., 1995;6:363-87.
Kaneko et al., J. Miol. Biol., 2000;295:997-1007.
Peretz et al., Nature, 2001;412:739-743.
E Cunha-Neto et al., PNAS, 1995;92:3541-3545.
E. Cunha-Neto et al., J. Clin. Invest., 1996;98:1709-1712.
Chabalgoity et al., Vaccine, 2000;19:460-469.
Pasetti et al., Clin. Immunol., 1999;92:76-89.
Hoiseth et al., Nature, 1981;291:238-239.
Chatfield et al., Vaccine, 1992;10:53-60.
Benkirane et al., J. Biol. Chem., 1993;268:26279-26285.
Ben-Yedidia et al., Mol. Immunol., 2002;39:323-331.
Ripka et al., Curr. Opin. Chem. Biol., 1998;2:441-452.
Spatola, In: Chem. Biochem. Amino Acids, Pept., Proteins; Weinstein, B., Ed.; Marcel Dekker: New York, 1983; pp. 267-357.
Hart and Rich, In: Pract. Med. Chem.; Wermuth, C., Ed., Acad. Press: London, U.K., 1996; pp. 393-412.
Farmer, In: Drug Design; Ariens, E.J., Ed.; Academic Press: New York, 1980; 10:119-143.
Fletcher and Campell, Chem. Rev., 1998;98:763-795.
Chabalgoity et al.. Exp. Rev. Vaccines, 2002;1:495-505.
Mastroeni et al., Veterinary Journal, 2001;161:132-164.
Cardenas and Clements, Clin. Microbiol. Rev., 1992;5:328-342.
Clements et al., 1992, In: Recombinant DNA Vaccines: Rationale and Strategy, Isaacson (ed.), Marcel Decker, New York. pp. 293-322.
Clements and Cardenas, Res. Microbiol., 1990;141:981-993.
Sanitago et al., Pharmaceutical Research, 1993;10:1243-1247.
Alving et al., Vaccine, 1986;4:166-172.
Garcon and Six, J. Immunol., 1991;146:3697-3702.
Gould-Fogerite and Mannino, 1993, In: Liposome Technology 2nd Edition. vol. III, Gregoriadis (ed.)).
Mowat and Donachie, Immunology Today, 1991;12:383-385.
Baylor, NW et al., Vaccine, 2002;20 Suppl 3:S18-23.
Clements et al., Vaccine, 1988;6:269-277.
Elson, Immunology Today, 1989;146:29-33.
Lycke and Holmgren, Immunology, 1986;59:301-308.
Lycke et al., Eur. J. Immunol., 1992;22:2277-2281.
Tamura et al., Japanese Journal of Infectious Diseases, 2000;53:98-106.
Finkelstein and LoSpalluto, J. Exp. Med., 1969;130: 185-202.
Elson and Ealding, J. Immunol., 1984;133:2892-2897.
Fujihashi et al., Acta Odontologica Scandinavica, 2001;59:301-308.
Czerkinsky et al., Proc. Natl. Acad. Sci. (USA), 1989;57:1072-1077.
Pierce et al., Infect. Immun., 1983;40: 1112-1118.
Cebra et al., 1986, In: Vaccines 86, Brown et al. (ed.), Cold Spring Harbor Laboratory, New York. pp. 129-133.
McKenzie and Halsey, J. Immunol., 1984;133: 1818-1824.
McCarthy et al., J. Immunol. Methods, 1985;82:349-358.
McCarthy D.A. and Drake, A.F., Mol. Immunol., 1989;26(9):875-881.
Tacket etal., Infection and Immunity, Mar. 2000;68(3):1196-1201.
Kotloff et al., Infect. Immun., 2002;70:2016-21.
Lillard et al., Cellular and Molecular Biology, 2001;47:1115-1120.
Levine et al., Journal of Biotechnology, 1996;44:193-196.
Nardelli-Haefliger et al., Infection and Immunity, 1996;64:5219-5224.
Tacket et al., Infection and Immunity, 1997;65:452-456.
O'Hagan et al. (Immunology 1991;73:239-42.
Sigurdsson et al. (Am J Pathol 2001;159:439-447.
Sobotka et al., Pharmacology, 1978;16:287-294.
Quartermain et al., Neurosci. Lett., 2000;288:155-158.
Ammassari-Teule et al., Behav. Brain Res., 1985;17:9-16.
Roullet et al., Physiol. Behav., 1998;64:203-7.
Roullet et al., Physiol. Behav., 1995;58:1189-95.
Knobel et al., J. Wildl. Dis., 2002;38:352-62.
Carp and Rubenstein, Semin. Virol 1991;2:203-213.
Kascsak et al., J Virol, 1986;59: 676-683.
Sigurdsson et al., TIMM, 2002;8:411-413.
Chabalgoity et al., Mol Microb., 1996;19(4):791-801.
Clements and El-Morshidy, Infect. Immun., 1984; 46:564-569.
M. H. Groschup et al. "Studies on Species-specific Epitope in Murine, Ovine and Bovine Prion Protein" Journal of General Virology, 1993, vol. 74, pp. 1451-1456.
Wei Shi, et al., "Papillomavirus Pseudovirus: a Novel Vaccine to Induce Mucosal and Systemic Cytotoxic T-Lymphocyte Responses", Journal of Virology, 2001, 75(21): 10139-10148.
Catherine Dupuy, et al., "Cell mediated immunity induced in mice by HPV 16 L1 virus-like particles", Microbial Pathogenesis 1997, 22: 219-225.
Thomas Wisniewski, et al., "Is vaccination against transmissible spongiform encephalopathy feasible?" Rev. sci. tech. Off. int. Epiz., 2007, 26(1): 243-251.
Thomas Wisniewski and Allal Boutajangout, "Vaccination as a Therapeutic Approach to Alzheimer's Disease", Mount Sinai Journal of Medicine, 2010, 77: 17-31.
Pierre Aucouturier et al., "Prion Diseases and the Immune System", Clinical Immunology, 2000, 96(2): 79-85.
Gottwein et al. (2001) J. Infect. Dis.; 184:308-314.
Heeger et al. (2000) J. Immunol.; 164;5771-5781.
Caughey et al., (1991); Biochemistry; 30:7672-7680.
Czerkinsky et al. (1999) Mucosal Immunity and Tolerance: Relevance to Vaccine Development; Immunological Reviews; 170:197-222.
Scheibner et al. "Vaccines" Nexus (2000) 8(1) (available online at www.whale.to/vaccine/adjuvants.html).
Zhang et al. (1997) "Physical Studies of Conformational Plasticity in a Recombinant Prion Protein" *Biochemistry* 36:3543-3553.
Telling et al. (1995) "Prion Propagation in Mice Expressing Human and Chimeric PrP Transgenes Implicates the Interaction of Cellular PrP with Another Protein" *Cell*, 83:79-90.
Hornemann et al. (1998) "Recombinant full-length murine prion protein, mPrP(23-231): purification and spectroscopic characterization" FEBS Letters 413(2)277-281.
Williamson et al. (1996) "Circumventing tolerance to generate autologous monoclonal antibodies to the prion protein" *Proc. Natl. Acad. Sci. USA* 93: 7279-7282.
Goni et al. (2008) "High titers of mucosal and systemic anti-PrP antibodies abrogate oral prion infection in mucosal-vaccinated mice" *Neuroscience* 153:679-686.
Goni et al. (2005) "Mucosal vaccination delays or prevents prion infection via an oral route" *Neuroscience* 133:413-421.
Radiation Safety Data Sheet from Canadian Nuclear Safety Commission. Dated Apr. 5, 2004. Downloaded from http://hr.lakeheadu.ca/uploads/S-35.pdf on Jul. 28, 2011.
Product Description for Rnase inhibitor, Rnasin, downloaded from http://www.dongshengbio.com/en/UploadFiles/2011321172230317.pdf on Jul. 28, 2011.

(56) References Cited

OTHER PUBLICATIONS

Chesebro et al. (1993) "Foreign PrP expression and scrapie infection in tissue culture cell lines" *Dev Biol Stand.* 80:131-40.
"Guidelines for the Research Use of Adjuvants", published by the National Institutes of Health, available online at http://oacu.od.nih.gov/ARAC/documents/Adjuvants.pdf (Nov. 14, 2007).
"Guidelines for Immunization of Research Animals," published online at http://www.ahc.umn.edu/ra/immun.html (Aug. 19, 2010).
"Use of Complete Freund's Adjuvant in Laboratory Animals," published by the University of Pennsylvania and available online at http://www.upenn.edu/regulatoryaffairs/Pdf/3UseOfCompleteFreundAdjuvant.pdf (Mar. 25, 2008).

* cited by examiner

|          | 228 | 229 | 230 | 231 | 232 | 233 | 234 | 235 | 236 | 237 | 238 | 239 | 240 | 241 | 242 | 243 | 244 | 245 | 246 | 247,248 | 249 | 250 | 251 | 252 | 253 |
|---|---|---|---|---|---|---|---|---|---|---|---|---|---|---|---|---|---|---|---|---|---|---|---|---|---|
| Human | R | Q | S | S |   | M | V | L | F | S | S | P | P | V | I | L | L | I | S | F | L | I | F | L | I | Y | G |
| Gorilla | R | Q | S | S |   | M | V | L | F | S | S | P | P | V | I | L | L | I | S | F | L | I | F | L | I | V | G |
| Chimpanzee | R | Q | S | S |   | M | V | L | F | S | S | P | P | V | I | L | L | I | S | F | L | I | F | L | I | V | G |
| Mouse | R | R | S | S | S | T | V | L | F | S | S | P | P | V | I | L | L | I | S | F | L | I | F | L | I | V | G |
| Rat | R | R | S | S |   | A | V | L | F | S | S | P | P | V | I | L | L | I | S |   | L | I | F | L | I | V | G |
| Syrian Hamster | R | R | S | S |   | A | V | L | F | S | S | P | P | V | I | L | L | I | S | F | L | I | F | L | M | V | G |
| Mink | R | Q | A | S |   | A | I | L | F | S | P | P | P | V | I | L | L | I | S | L | L | I | L | L | I | V | G |
| Sheep | R | Q | A | S |   | V | I | L | F | S | S | P | P | V | I | L | L | I | S | F | L | I | F | L | I | V | G |
| Goat | R | Q | A | S |   | V | I | L | F | S | P | P | P | V | I | L | L | I | S | L | L | I | L | L | I | V | G |
| Cow | R | Q | A | S |   | V | I | L | F | S | S | P | P | V | I | L | L | I | S | F | L | I | F | L | I | V | G |
| Greater Kudu | R | G | A | S |   | V | I | L | F | S | S | P | P | V | I | L | L | I | S | F | L | I | F | L | I | V | G |

Fig. 1C

MUCOSAL IMMUNIZATION TO PREVENT PRION INFECTION

CROSS REFERENCE TO PRIOR APPLICATION

This is a U.S. National Phase application under 35 U.S.C. §371 of International Patent Application No. PCT/US2004/16242, filed May 20, 2004, which claims priority to U.S. Provisional Patent Application Ser. No. 60/472,262, filed on May 20, 2003. The International Application was published on Mar. 3, 2005 as WO 2005/019412 A2 under PCT Article 21(2).

FIELD OF THE INVENTION

This invention relates to methods and compositions for inducing an immune response to prion proteins and deposits, and for vaccinating humans and other animals against prion disease.

BACKGROUND OF THE INVENTION

Neurodegenerative disorders are becoming increasingly common and an ever greater health care burden, as the average age in Western populations rises. The most common of these illnesses is Alzheimer's disease (AD), of which there are now about 5 million cases in the U.S. alone. Prion diseases (or prionoses) represent another neurodegenerative category, which currently is more rare than AD. However, the recent emergence of new variant Creutzfeldt-Jakob (nvCJD) has raised the possibility of a larger population at risk for this illness, as well as causing great concern regarding the safety of blood bank supplies (Jackson and Collinge, Mol Pathol. 2001; 54:393-9).

The term prionosis is used to describe any disease linked to conditions affecting the prion protein, also termed transmissible spongiform encephalopathies. The first prionosis to be described was scrapie, a disease of sheep recognized for over 250 years. The first identified human prionosis; kuru, is an illness of the Fore people living in the highlands of New Guinea (Gajdusek and Zigas, N. Eng. J. Med., 1957; 257:974-978; Gajdusek and Zigas, Am. J. Med., 1959; 26:442-469). Kuru is thought to be linked to ritualistic cannibalism. The most well-known of the human prionoses, Creutzfeldt-Jacob disease (CJD), initially described by in 1921, is found throughout the world with an incidence of about 1 per million. In addition to extensive cortical spongiosis (i.e., vacuolation of the brain parenchyma), gliosis (i.e., dense fibrous network of neuroglia) and neuronal loss, 10% of CJD cases are characterized by amyloid plaques (Prusiner et al., Prion Protein Biology, 1998; 93:337-348).

Other human prionoses include the autosomal dominantly inherited Gerstmann-Sträussler-Scheinker disease (GSS), described in a large kindred in 1936 (Gerstmann et al., Z Neurol., 1936; 154:736-762), and prion protein-congophilic angiopathy (PrP-CAA) (Ghetti et al., Proc. Natl. Acad. Sci. USA, 1996; 93:744-748). The neuropathological features of PrP-CAA as well as some kindreds of GSS (Ghetti et al., Mol. Neurobiol., 1994; 8:41-48) include neurofibrillary tangles (NFT), which is an essential feature of AD. Congophilic angiopathy is also an essential feature of AD. Both these variants of prionoses further link the pathogenesis of AD and the prion related diseases.

Fatal familial insomnia (FFI) is a disorder presenting with intractable insomnia, dysautonomia, a variety of endocrine abnormalities and motor paralysis (Medori et al., N. Eng. J. Med., 1992; 326:444-449). Unlike other prionoses, spongiform change can be a minor feature or be absent altogether. AU patients with FFI have a missense mutation at codon 178 of the PrP gene where Asn is replaced by Asp, coupled with a Met at the polymorphic codon 129 (Goldfarb et al., Science, 1992; 258:806-808). The somewhat divergent clinical and neuropathological features of FFI, in comparison to other human prionoses, highlight the wide spectrum of disease associated with PrP dysfunction and suggests that there may be other human illnesses which have yet to be recognized as prionoses.

In cattle, there has been a recent epidemic of a new prionosis, bovine spongiform encephalopathy (BSE), that has led to more than 160,000 cattle deaths in the UK (Collinge, Hum. Mol. Genet, 1997; 6:1699-1705). This new disease is thought to be caused by meat and bone meal dietary supplements to cattle that were contaminated with scrapie infected sheep and other cattle with BSE. Some evidence suggests that BSE also has led to a new type of CJD, called new variant CJD (vCJD) (Collinge et al., Nature, 1996; 383:685-690). The first cases of vCJD were reported in 1995, when two cases of CJD were found in 2 British teenagers These cases had distinctive neuropathology that included so-called "florid" amyloid plaques which are reminiscent of kuru-associated PrP amyloid plaques (Collee and Bradley, Lancet, 1997; 349:636-641; Will et al., Lancet, 1997; 347:921-925). Since the original reports, there have been 14 cases with these distinctive features; all were in the UK except for one French case. The emergence of vCJD has raised the specter of an epidemic of prion related disease among the British population similar to that of BSE in cattle.

Prion disease is also found among wild animals. The disease, termed chronic wasting disease (CWD), attacks the brains of infected deer and elk, causing the animals to become emaciated, display abnormal behavior, lose bodily functions and die. The incidence of CWD in wild animals is of great concern. The disease was originally described in captive animals 35 years ago in Colorado. However, over the last five years, the disease has been found in wild herds in several surrounding states and Canada, and in early 2002, CWD was detected in wild deer in South Dakota, Wisconsin and New Mexico. The recent detection of CWD in the wild white-tailed deer herd in Wisconsin is of particular concern, since white-tailed deer appear more susceptible than muledeer and elk to CWD with a greater percentage of the herd becoming infected.

The most widely accepted hypothesis regarding the etiology of the prionoses is that the disease is caused by a protein or a "prion" (as in proteinous infectious particle) (Griffith, Nature, 1967; 215:1043-1044; Prusiner, Science, 1982; 216: 136-144, Prusiner et al., Prion Protein Biology, 1998; 93:337-348). According to this hypothesis, a prion is a conformationally modified form, termed $PrP^{Sc}$, of a normal cellular protein, termed $PrP^C$, which is a normal host protein found on the surface of many cells, particularly neurons. $PrP^C$ and $PrP^{Sc}$ are thought to differ only in their conformation, with $PrP^C$ having a greater β-sheet content. When introduced into normal, healthy cells, $PrP^{Sc}$ causes the conversion of $PrP^C$ into additional $PrP^{Sc}$ molecules, initiating a self-perpetuating vicious cycle (Prusiner et al., Prion Protein Biology, 1998; 93:337-348). The etiology of prion diseases is thus the conversion of the normal prion protein, $PrP^C$, into its infectious and pathogenic form, $PrP^{Sc}$ (Prusiner et al., Prion Protein Biology, 1998; 93:337-348; Horwich and Weismann, Cell, 1997; 89:499-510).

The human PrP gene spans 20 kb and consists of a short, non-coding first exon, a 10-15 kb intron and a second exon that contains the entire 759 bp open reading frame encoding a 253 amino acid protein, and 1.64 kb of 3' non-translated sequence (SEQ ID NO:1). The identification of the PrP gene, designated PRNP in humans, also allowed for the characterization of numerous mutations associated with familial prionoses (Prusiner et al., Prion Protein Biology, 1998; 93:337-348). Moreover, the PrP gene is highly conserved across mammalian species (see FIG. 1), and sequenced prion proteins include those of cow (SEQ ID NO:2); deer (SEQ ID NO:3); elk (SEQ ID NO:4), and muledeer (SEQ ID NO:5) (Cervenakova et al., Lancet, 1997; 350:219-90; Kaluz et al., Gene, 1997; 199:283-6); mouse (SEQ ID NO:6) and rat (SEQ ID NO:7); sheep (SEQ ID NO:8) and goat (SEQ ID NO:9); Syrian hamster (SEQ ID NO:10) and mink (SEQ ID NO:11); gorilla (SEQ ID NO:12) and chimpanzee (SEQ ID NO:13; Greater Kudu (SEQ ID NO:14); camel (SEQ ID NO:15); and pig (SEQ ID NO:16). Prion proteins in mammals are constitutively expressed in both neuronal and non-neuronal tissue (Kretzschmar et al., Am. J. Pathol., 1986; 122:1-5), and while the highest mRNA levels are found in neurons, in particular in the hippocampus, substantial amounts are also found in the heart and skeletal muscle.

Currently, there are no effective treatment or prevention methods for prion disease in humans or other animals, and only a limited number of approaches have been attempted. Experimental treatment approaches reported include the use of amphotericin B (Pocchiari et al., J. Gen. Virol., 1987; 68(Pt 1):219-223), Congo red (Caughey and Race, J. Neurochem., 1992; 59:768-771), sulphated polyanions (Ladogana et al., J. Gen. Virol., 1992; 73(Pt 3):661-665), anthracyclines (Tagliavini et al., Science, 1997; 276:1119-1122), β-sheet breaker peptides (Soto et al., Lancet, 2000; 355:192-197), porphyrin and phthalocyanine compounds (Priola et al., Science, 2000; 287:1503-1506). Some of these compounds delay the incubation time of animals infected with PrP$^{Sc}$ but all have limitations in terms of toxicity and/or pharmacokinetics.

It has long been known that there is no specific immune response against prions, and the immune system appears to help rather than impair the propagation of prions (Aucouturier et al., Clin. Immunol, 2000; 96:79-85; Aucouturier et al., J. Clin. Invest., 2001; 108:703-708). However, therapeutic approaches based on the elicitation of an immune response against prion disease have been suggested (see, e.g., co-pending application PCT/US02/37634, filed Nov. 21, 2002, hereby incorporated by reference in its entirety, and by Wisniewski et al. (Curr. Neurosci Reports 2002; 2:400-4) and Wisniewski et al. (Biochem. Soc. Transact. 2002; 30:574-578)). Experimental studies in mouse models found that animals vaccinated intraperitoneally with recombinant mouse prion protein (rPrP) and complete Freund's adjuvant had a delay in the onset of prion disease, regardless of whether the vaccination was performed prior to or after peripheral prion exposure (Sigurdsson et al., Am J Pathol 2002; 161:13-17). In addition, anti-prion antibodies administered intraperitoneally post-inoculation of scrapie strain 139A increased the time from inoculation to onset of disease in experimental animals (Sigurdsson et al., Neurosci Lett, 2003; 336:185-7).

Active immunization has recently been tried in humans for another conformational disease; AD, however, significant toxicity resulted from the vaccine (Steinberg, New Scientist, 2002; 16:22; Munch et al., J. Neural Transm., 2002; 109: 1081-1087; Schenk, Nat. Rev. Neurosci., 2002; 3:824-828). For example, in the human phase 2A clinical trial of the AD vaccine, 15 out of 360 patients worldwide developed symptoms of central nervous system inflammation, with symptoms apparently responding to immunosuppression in most patients (Steinberg, New Scientist, 2002; 16:22; Munch et al., J. Neural Transm., 2002; 109:1081-1087; Schenk, Nat. Rev. Neurosci., 2002; 3:824-828). One possible problem of the vaccine was that fibrillar Aβ1-42, an innately toxic peptide, was used. Also, the AD vaccine was administered subcutaneously with an adjuvant (saponin QS-21) that primarily stimulates cell mediated immunity (White et al., Adv. Exp. Med. Biol., 1991; 303:207-210), and the cerebral inflammation seen in the patients vaccinated appeared to be related to activation of CD8-positive cytotoxic T-cells within the central nervous system (Munch et al., J. Neural Transm., 2002; 109: 1081-1087). These results emphasize the difficulties in designing safe and effective vaccines for AD and other conformational diseases.

Accordingly, there is a need for safe and efficient therapeutic and preventive methods for prion diseases. The invention addresses these and other needs in the art.

SUMMARY OF THE INVENTION

The present invention is based on vaccine compositions for prion disease which primarily induce a humoral immune response, i.e., antibody response. The invention is also based on mucosal administration regimens of such vaccines, designed to primarily induce a humoral immune response against the prion protein.

Accordingly, the present invention provides a vaccine composition comprising a mammalian prion protein and an adjuvant eliciting a humoral immune response. Preferably, the prion protein is a human, bovine, deer, elk, or sheep prion protein. Alternatively, the prion protein can comprise a fragment of human, bovine, deer, elk, or sheep prion protein. For example, residues 90-144 of SEQ ID NO:1; residues 112-214 of SEQ ID NO:1; residues 93-156 of SEQ ID NO:2, SEQ ID NO:3, SEQ ID NO:4, or SEQ ID NO:8; or residues 123-225 of SEQ ID NO:2, SEQ ID NO:3, SEQ ID NO:4, or SEQ ID NO:8. In one embodiment, all amino acid residues in the prion protein are D-amino acids. In another embodiment, the prion protein comprises at least one homolog of residues 90-144 of SEQ ID NO:1 wherein at least one of residues 121, 122, 128, 129, and 130 has been substituted with Pro, Asp, Glu, Lys, Gly, Ser or Cys. In a further embodiment, the prion protein comprises at least one homolog of residues 112-214 of SEQ ID NO:1 wherein at least one of residues 112, 116, 117, 118, 121, 122, 128, 129 and 130 has been substituted with Pro, Asp, Glu, Lys, Gly, Ser or Cys. The amino acids of the homologs may be L- or D-amino acids and the homologs may further comprise an N- and/or C-terminal sequence of 4-10 Lys or Asp residues. In a particular embodiment, the adjuvant is cholera toxin subunit B (CT-B) or non-toxic derivatives of either cholera toxin (CT) or heat-labile enterotoxin (LT) of *Escherichia coli*. The prion protein may, for example, be covalently attached to the cholera toxin subunit B.

The invention also provides for a method of preventing or treating a prion disease, comprising mucosal administration of a vaccine comprising a mammalian prion protein and an adjuvant eliciting a humoral immune response to a mammalian subject in need thereof. The mammalian subject can, for example, be a member of the group consisting human, bovine, elk, sheep, and deer, including, but not limited to, red deer, *Cervus elaphus*, or mule deer, *Odocoileus hemionus*. The vaccine may be mucosally administered by, for example, oral, intragastric, intranasal, rectal and intraocular administration. In one embodiment, the subject is human and the prion disease is Creuzfeldt-Jakob's Disease, variant Creuzfeldt-Jakob's Disease, Gerstmann-Sträussler-Scheinker disease, prion protein-congophilic angiopathy, and familial fatal insomnia. In another embodiment, the subject is bovine and the prion disease is bovine spongiform encephalopathy. In another embodiment, the subject is sheep and the prion disease is scrapie. In yet another embodiment, the subject is deer and the prion disease is chronic wasting disease. The method may further comprise repeating the mucosal administration at least once. For example, the mucosal administration can be repeated at least once, preferably twice, within one month after the first administration.

The invention also provides for a vaccine composition comprising an attenuated strain of *Salmonella* spp bacterium transfected with a vector capable of expressing a mammalian prion protein. Preferably, the prion protein is a human, bovine, deer, elk, or sheep prion protein. Alternatively, the prion protein can comprise a fragment of human, bovine, deer, elk, or sheep prion protein. For example, residues 90-144 of SEQ ID NO:1; residues 112-214 of SEQ ID NO:1; residues 93-156 of SEQ ID NO:2, SEQ ID NO:3, SEQ ID NO:4, or SEQ ID NO:8; or residues 123-225 of SEQ ID NO:2, SEQ ID NO:3, SEQ ID NO: 4, or SEQ ID NO:8. In one embodiment, all amino acid residues in the prion protein are D-amino acids. In another embodiment, the prion protein comprises at least one homolog of residues 90-144 of SEQ ID NO:1 wherein at least one of residues 121, 122, 128, 129, and 130 has been substituted with Pro, Asp, Glu, Lys, Gly, Ser or Cys. In another embodiment, the prion protein comprises at least one homolog of residues 112-214 of SEQ ID NO:1 wherein at least one of residues 112, 116, 117, 118, 121, 122, 128, 129 and 130 has been substituted with Pro, Asp, Glu, Lys, Gly, Ser or Cys. The amino acids of the homologs may be L- or D-amino acids and the homologs may further comprise an N- and/or C-terminal sequence of 4-10 Lys or Asp residues. In a particular embodiment, the *Salmonella* bacterium is of a strain selected from *Salmonella typhimurium, Salmonella enteritidis, Salmonella dublin* or *Salmonella typhi*.

In a particular embodiment a priming dose could be parenterally injected by intradermal, subcutaneous, intramuscular, or intravenous routes, followed by mucosal (e.g., oral, nasal, intragastric, rectal, or intraocular) boostings (Lauterslager et al., Vaccine, 2003; 21:1391-1399).

The invention also provides for a method of preventing or treating a prion disease, comprising mucosal administration of a vaccine composition comprising an attenuated strain of *Salmonella* spp transfected with a vector capable of expressing a mammalian prion protein to a mammalian subject in need thereof. The mammalian subject can, for example, be a member of the group consisting human, bovine, deer, elk, and sheep. The vaccine may be mucosally administered by, for example, oral, intragastric, intranasal, rectal and intraocular administration. In one embodiment, the subject is human and the prion disease is Creuzfeldt-Jakob's Disease, variant Creuzfeldt-Jakob's Disease, Gerstmann-Sträussler-Scheinker disease, prion protein-congophilic angiopathy, and familial fatal insomnia In another embodiment, the subject is bovine and the prion disease is bovine spongiform encephalopathy. In another embodiment, the subject is sheep and the prion disease is scrapie. In yet another embodiment, the subject is deer and the prion disease is chronic wasting disease. The method may further comprise repeating the mucosal administration at least once. For example, the mucosal administration can be repeated at least once, preferably twice within one month after the first administration.

The invention also provides for a pharmaceutical composition comprising a mammalian prion protein, an adjuvant eliciting a humoral immune response, and a pharmaceutically acceptable excipient. The excipient may be, for example, sodium bicarbonate or aluminum based (alum) excipients.

The invention also provides for a pharmaceutical composition comprising an attenuated strain of *Salmonella* spp transfected with a vector capable of expressing a mammalian prion protein and a pharmaceutically acceptable excipient. The excipient may be, for example, sodium bicarbonate or aluminum based (alum) excipients, or any other suitable excipient which does not affect the conformation of the PrP or the viability of the *Salmonella*.

The above features and many other attendant advantages of the invention will become better understood by reference to the following detailed description when taken in conjunction with the accompanying drawings.

BRIEF DESCRIPTION OF THE DRAWINGS

FIGS. 1A-1C shows an alignment of amino acid sequences of prion protein (PrP) from human (SEQ ID NO:1), gorilla (SEQ ID NO:12), chimpanzee (SEQ ID NO:13), mouse (SEQ ID NO:6), rat (SEQ ID NO:7), Syrian hamster (SEQ ID NO:10), mink (SEQ ID NO:11), sheep (SEQ ID NO:8), goat (SEQ ID NO:9), cow (SEQ ID NO:2), and greater kudu (SEQ ID NO: 14). Amino acid residues that are identical and conserved among the prion proteins of the species presented in this figure are boxed.

DETAILED DESCRIPTION OF THE INVENTION

Figure 2:
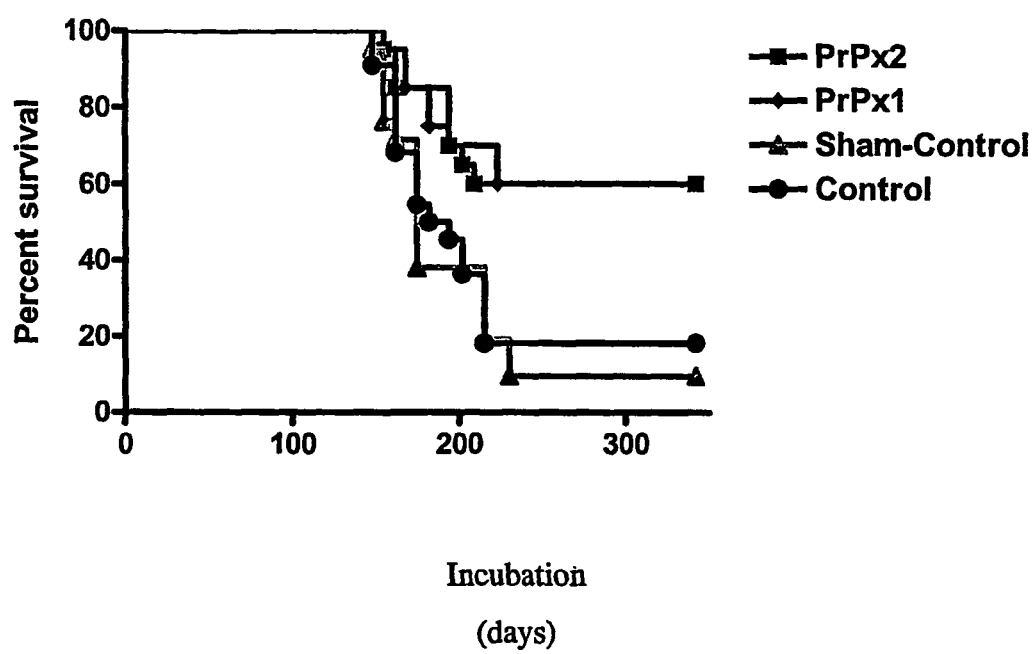
FIG. 2 shows a Kaplan-Meier survival curve for mice orally inoculated with PrP×2, PrP×1, sham-control or control.

The present invention describes an improved immunization strategy for prion disease. The compositions and methods of the present invention result in a prolonged incubation period and the prevention of symptomatic infection. The optimized active immunization approach makes vaccination against prion diseases efficient and safe for use in humans and other mammals. For example, the prion vaccine approach could be applied for immunizing the deer population to prevent the spread of chronic wasting disease in the USA, and for vaccinating the European human population, where extensive exposure to the BSE prion agent has occurred. As shown herein, using these methods and compositions, the entry of prions can be successfully hindered at their most common natural route of entry. In addition, mucosal immunity being predominantly associated with an IgA response and a systemic humoral T-helper type 2 CD4+ response, which induces mainly humoral and none or only minimal cell mediated immunity (Foss, Animal Health Research Reviews, 2000; 1:3-24), the safety of this type of vaccine is improved.

In one embodiment, a conjugate of prion protein and cholera toxin subunit B is administered to vaccinate against prion disease or to prolong the time of onset of the disease after exposure to prions. The cholera/PrP immunization produces a significant mucosal immune response that prevents prion infection following oral inoculation. In another embodiment, the prion protein immunogen is administered via a live vector, i.e., an attenuated *Salmonella* or *Shigella* host comprising a vector expressing the prion protein. Preliminary results indicate that a high level of murine prion protein expression is achieved using the *Salmonella typhimurium* strains LVR03 or SL3261 as vectors, and that CD-1 mice tolerate the vaccine with no toxicity. The adjuvant sodium bicarbonate was added to the vaccine to maintain a basic pH, which accelerated the passage of the vaccine from the stomach to the intestines where the vaccine is absorbed. In yet other embodiments, mucosal adjuvants such as non-toxic derivatives of heat-labile enterotoxin of *E. coli*; delivery vehicles such as proteosomes, liposomes; alum (e.g., aluminum hydroxide); molecular adjuvants such as CpG DNA. CpG is an oligodeoxynucleotide that has been shown to be an inducer of innate immunity, see Sethi et al., Lancet, 2002; 360:229-230. Vaccine delivery vehicles such as cochleates can also be used. Cochleates are stable phospholipids calcium precipitates distinct from liposomes, which provide protection for vaccines from harsh acid and degradative environments thereby allowing efficient delivery by mucosal routes (Mannino and Gould-Fogerite, Pharm. Biotechnol., 1995; 6:363-87). Selected active immunization approaches can be preclinically tested in transgenic mice expressing, e.g., human, bovine, or deer PrP.

The immunogen itself, the prion protein, can be the endogenous prion protein in the species for which the vaccine is intended, an orthologous prion protein, a prion protein homolog, or immunogenic fragments of any of these full-length proteins. For example, it has been reported that the region of residues 90-144 of human PrP is important for initiating prion disease (Kanecko et al., J. Miol. Biol., 2000; 295:997-1007), whereas residues 23-89 and 141-176 are not required for infectivity. Accordingly, the embodiment of a full-length prion protein with one to five amino acid substitutions retains the epitopes located at approximately residues 93-119, 145-174, and 172-201 that were previously reported to be effective in raising antibodies. Any substitutions made in the 90-144 region reported to be important in initiating prion disease in humans, which corresponds to the region of residues 93-156 in bovine PrP and residues 93 to 156 in deer PrP, is designed to replace residues that have a high propensity for forming β-sheets, such as Val, Ile, Tyr, Trp, Leu, Thr, Gln, and Met, according to Chou and Fasman with residues that have a low propensity for forming β-sheets, such as Pro, Glu, Asp, Lys, Gly, Ser or Cys. The choice of residues 121, 122, 128, 129, and 130 of human PrP and residues 132, 133, 139, 140, and 141 of bovine PrP for substitution with residues that have a low propensity for forming #-sheets (1) avoids disturbing epitopes identified to be effective in raising antibodies as well as the epitope at residues 132-140 of human PrP to which the binding of an antibody prevents formation of the abnormal scrapie form of prion protein ($PrP^{Sc}$) in vitro (Peretz et al., Nature, 2001; 412:739-743) and (2) results in a polypeptide that is immunogenic but has a much reduced propensity for forming toxic prion deposits. The same methodology can be applied to design PrP fragments or homologs for vaccines for other species, e.g., deer, elk, and sheep. Substitution of residues 112, 116, 117 and 118 of human PrP with residues that have a low propensity for forming β-sheets, such as Pro, Glu, Asp, Lys, Gly, Ser or Cys, eliminates an epitope in the region 115-120 that is known to be responsible for autoimmune cardiomyopathy in humans (E. Cunha-Neto et al., PNAS, 1995; 92:3541-3545; E. Cunha-Neto et al., J. Clin. Invest., 1996; 98:1709-1712).

Definitions

The following defined terms are used throughout the present specification, and should be helpful in understanding the scope and practice of the present invention.

The term "subject" means a mammalian subject which is at risk for exposure to prions or for developing prion disease, including, without limitation, humans, deer, elk, cows, sheep, hamsters, camel, gorilla, chimpanzee, Greater Kudu, mice, and rats. In the case of experimental animals, transgenic animals expressing a heterologous prion protein are also contemplated.

An "adjuvant" as used herein means a substance that augments, stimulates, activates, or potentiates an immune response against a prion protein at either the cellular or humoral level. The adjuvant may be conjugated or cross-linked to the immunogen. Alternatively, the adjuvant is not conjugated to the prion protein but is added as an exogenous adjuvant/emulsion formulation which maximizes mucosal immune responses to the prion protein. Preferred adjuvants are those which are shown to promote mucosal immunity with minimal or at least acceptable side effects. For human use, preferred adjuvants are those which have been successfully used in Phase I trials, lack reactogenicity in preclinical safety studies, have potential for approval for use in humans, or have been approved for use in food and companion animals.

An "attenuated" microorganism is an organism with reduced virulence (infectivity). Because of their reduced virulence, attenuated microorganisms are suitable for use as antigen delivery vectors (sometimes with adjuvant properties) in vaccines. Methods for attenuating microorganisms are well known in the art. See, e.g., Chabalgoity et al., (Vaccine, 2000; 19:460-469); Pasetti et al. (Clin Immunol 1999; 92:76-89) and Hoiseth et al. (Nature, 1981; 291:238-239) for attenuated *S. typhimurium* strains, and Chatfield et al. (Vaccine, 1992; 10:53-60) for attenuated *S. typhi* strains.

"Amyloidosis" as used herein refers to the deposition of insoluble, fibrous amyloid (or "aggregate") proteins, which are predominantly found extracellularly in organs and tissues. Amyloid fibrils can consist of various amino acid sequences, but, in general, all share β-pleated-sheet (or "β-sheet") secondary structure. The amyloidosis found in prionoses are caused by prion protein deposits.

The term "immunoeffective amount" of a prion protein, adjuvant, or vaccine refers to a nontoxic but sufficient amount of a compound to provide the desired mucosal immune response at a reasonable benefit/risk ratio attending any medical treatment. The immunoeffective amount of a compound can be estimated initially either in vitro or in animal models, usually mice, rabbits, guinea pigs, dogs, or pigs. The animal model is also used to achieve a desirable concentration range and route of administration. Such information can then be used to determine useful doses and routes for administration in humans. The efficacy and toxicity of a compound can be determined by standard pharmaceutical procedures in cell cultures or experimental animals, e.g., $ED_{50}$ (the dose leading to the desired effect in 50% of the population) and $LD_{50}$ (the dose lethal to 50% of the population). A pharmaceutically useful dosage lies preferably within a range that includes the $ED_{50}$ with little or no toxicity. The dosage varies depending upon the disease or condition to be treated or prevented, dosage form employed, sensitivity of the patient, and the route of administration.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value.

In accordance with the present invention there may also be employed conventional molecular biology, microbiology, and recombinant DNA techniques within the skill of the art. The general genetic engineering tools and techniques discussed herein, including transformation and expression, the use of host cells, vectors, expression systems, etc., are well known in the art. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al. 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Prion Protein

A "prion protein" or "prion peptide" means a protein or peptide comprising an amino acid sequence at least 80%, at least 85%, at least 90%, at least 95%, 96%, 97%, 98%, 99% or 100% identical to an amino acid sequence unique to the prion protein, or fragment thereof, in the species for which the vaccine is intended. Naturally occurring prion proteins include, but are not limited to, prion protein in humans (SEQ ID NO:1); cows (bovine prion protein) (SEQ ID NO:2); deer (SEQ ID NO:3); mouse prion protein (SEQ ID NO:6); rats (SEQ ID NO:7), sheep (SEQ ID NO:8), and elk (SEQ ID NO:4). An alternative to full-length PrP for use in a prion vaccine is a segment of the sequence containing at least residues 90 to 144 of human prion protein (SEQ ID NO:1) or at least residues 93 to 156 of bovine prion protein (SEQ ID NO:2) or deer/elk (SEQ ID NO:3 and 4, respectively). In one embodiment, the prion protein or fragment is modified to be N- or C-terminally coupled to a polylysine or polyaspartate segment. In another embodiment, the C-terminal residue of a prion protein may be amidated.

Prion proteins can be prepared using any method known in the art, including purification from amyloid lesions in animal tissues, synthesizing peptides using known peptide synthetic techniques, or recombinant expression in cultured cells.

Antibodies to peptides wherein the amino acids are in D-form (i.e., D-amino acids) recognize also the corresponding L-form peptide, and vice versa (Benkirane et al., J. Biol. Chem., 1993; 268:26279-85). Accordingly, in one embodiment of the vaccine comprising prion homologs according to the present invention, all residues of the peptide are D-amino acids. The amino acids being in D-form would also have the effect of enhancing the stability of the peptide. These D-amino acids can be in the same order as the L-form of the peptide or assembled in a reverse order from the L-form sequence to maintain the overall topology of the native sequence (Ben-Yedidia et al., Mol. Immunol., 2002; 39:323). The reduced fibrillogenic or reduced deposit-forming potential for the synthetic polypeptide or peptide can be readily determined by measuring the β-sheet conformation of the polypeptides/peptides using conventional techniques such as circular dichroism spectra, FT-IR, and electron microscopy of polypeptide or peptide suspensions.

Figure 1A:
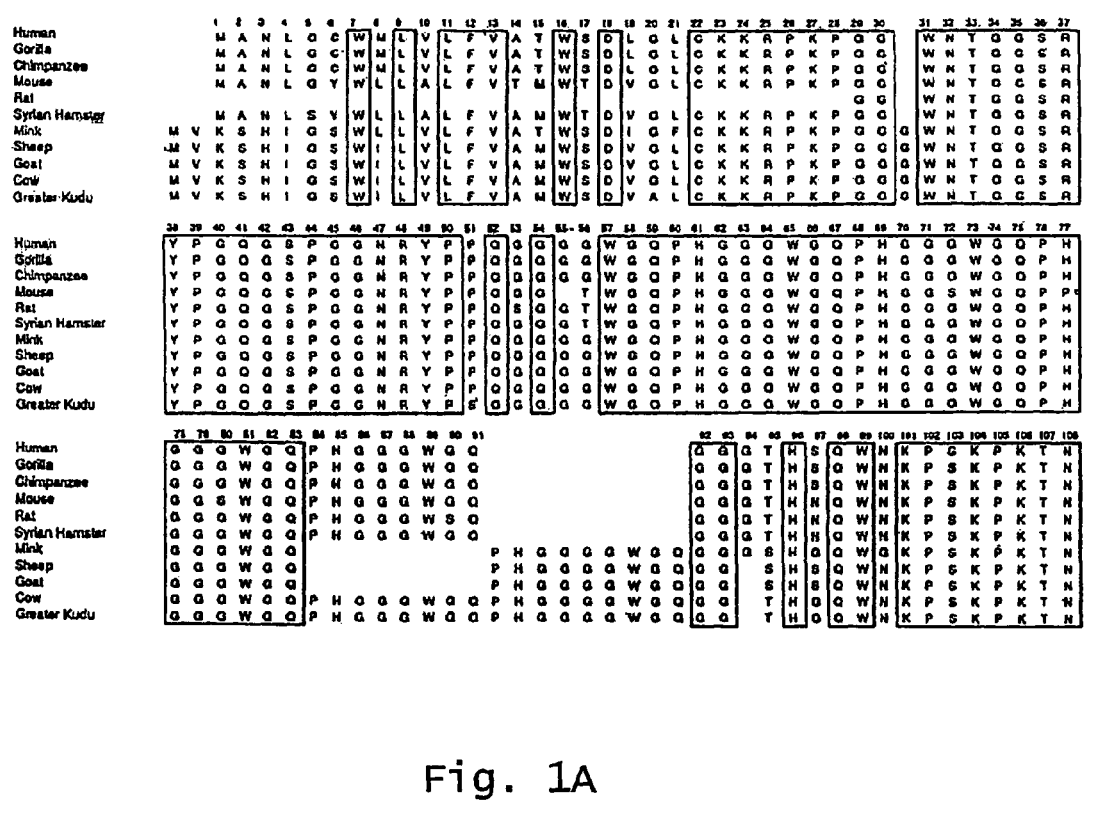

In a particular embodiment, the invention provides immunizing compositions for a mammal based on an orthologous prion protein. It is expected that mammals which are not closely related do not transmit prion disease to each other. For example, mammalian species such mouse, rat, sheep, goat, mink, Syrian hamster, and greater Kudu (an antelope) are not likely to transmit prion disease to humans, and vice versa Thus, an immunizing composition with a prion protein or an immunogenic fragment thereof from a mammalian species, can be administered to a mammalian subject from another species which is not closely related, to immunize against endogenous prion disease. From the amino acid alignment shown in FIG. 1, a prion protein where the conserved amino acid residues that correspond to those amino acids substituted in the modified human PrP of SEQ ID NO:1 are likewise substituted, and can also be administered to a human or mammalian subject to induce an immune response to prion protein and prion deposits. For instance, conserved residues 120, 121, 127, 128, and 129 of mouse PrP correspond to residues 121, 122, 128, 129, and 130 of human PrP and can be likewise substituted. Orthologues can also be N- or C-terminally coupled to a polylysine or polyaspartate tail of about 4-10 residues, or the C-terminal may be amidated.

Similarly, in a method for inducing an immune response to PrP and prion deposit in a bovine, deer, or elk subject, an immunizing composition with a synthetic immunogenic but non-deposit-forming polypeptide/peptide homologous to bovine, deer, or elk PrP according to the present invention or an immunizing composition with a prion protein, or immunogenic fragment thereof, from a mammalian species that does not transmit prion disease to cows, deer, or elk can be administered. The prion protein or fragment thereof from a mammalian species that does not transmit prion disease to the species in question may be modified at either or both termini or at the corresponding conserved amino acid residues according to the synthetic immunogenic but non-depositing forming polypeptide/peptide homologous to bovine PrP.

Synthetic non-deposit-forming prion proteins/peptides homologous to prion protein (PrP) can be used as an antigenic source. The peptide homologues have a reduced ability to adopt a α-sheet conformation, and have a lower risk of leading to any toxic effects in humans. By using these synthetic non-depositing-forming peptides, antibodies thereto, or conjugates thereof, in an immunizing composition, the present invention provides a means for rendering prion proteins and deposits targets for the immune system. The amino acids in these peptides may be in either L- or D-form. D-form peptides can have a higher stability than L-form peptides in vivo. The non-amyloidogenic prion protein or fragment can also be N- or C-terminally coupled to a polylysine or polyaspartate segment. In another embodiment, the C-terminal residue of a non-amyloidogenic prion protein may be amidated.

Prion proteins also include synthetic peptides which are homologous to a naturally occurring prion protein or a fragment thereof, but are "non-amyloidogenic", i.e., do not form amyloid deposits. For human and bovine prion protein such homologs include the full-length prion protein where at least one of residues 112, 116, 117, 118, 121, 122, 128, 129, and 130 of human prion protein (PrP) or of residues 123, 127, 128, 129, 132, 133, 139, 140, and 141 of bovine prion protein is substituted with Pro, Glu, Asp, Lys, Gly, Ser or Cys; a fragment of the modified full-length prion protein of containing at least residues 90-144 of human prion protein or residues 93-156 of bovine prion protein; and a peptide corresponding to residues 90-144 of human prion protein or to residues 93-156 of bovine/deer/elk prion protein in which at least one of residues 112, 116, 117, 118, 121, 122, 128, 129, 130 or 132, 133, 139, 140, 141, respectively, is substituted with Pro, Glu, Asp, Lys, Gly Ser or Cys. In addition, when more than one residue is to be substituted, it is preferred that the same amino acid residue is used for all substitutions.

For homologs of human, bovine, deer, and elk full-length PrP, one to five residues, preferably four or five residues, of human prion residues 112, 116, 117, 118, 121, 122, 128, 129, and 130, of SEQ ID NO: 1 or of bovine, deer, or elk prion residues 123, 127, 128, 129, 132, 133, 139, 140, and 141 of SEQ ID NO:2, SEQ ID NO:3, and SEQ ID NO:4, respectively, is substituted with Pro, Glu, Asp, Lys, Gly, Ser or Cys, more preferably Pro, Glu, Asp, or Lys. Exemplary homologs of full-length human and bovine PrP can be found in SEQ ID NOS:17 and 18, respectively.

The synthetic immunogenic but non-deposit-forming peptide homologous to human or bovine PrP include peptides of residues 90 to 144 of SEQ ID NO:1 or residues 93 to 156 of SEQ ID NO:2 or fragments of the peptides, where one to five residues but preferably four or five residues are substituted, and/or a polylysine or polyaspartate of 4 to 10 residues in length is joined at the N-terminal and/or C-terminal end of the peptide. These embodiments can be described as follows:

$$(A)_m-(N—Xaa_1 Xaa_2 GlyGlyLeuGlyGly Xaa_3 Xaa_4 Xaa_5-C)_n—(B)_p$$

wherein m is 0, 4, 5, 6, 7, 8, 9, or 10; p is 0, 4, 5, 6, 7, 8, 9, or 10; A is Lys or Asp; B is Lys or Asp; n is 1 or 2; N represents residues 90-120 of SEQ ID NO:1; C represents residues 131-144 of SEQ ID NO:1; and $Xaa_1$, $Xaa_2$, $Xaa_3$, $Xaa_4$, and $Xaa_5$ are Val, Val, Tyr, Met, and Leu, respectively, in which zero to five, preferably four or five, of residues $Xaa_1$-$Xaa_5$ is substituted with Pro, Glu, Asp, Lys, Gly, or Ser ($(A)_m$-(N-SEQ ID NO:32-C)$_n$—$(B)_p$). This sequence corresponds to SEQ ID NO:32 with optional N- and/or C-terminal residues per below, and with optional polylysine or polyaspartic acid segments of 4-10 residues attached to the N- and/or C-terminal.

Where the peptide homologous to bovine, deer, or elk PrP is used for administration in the respective animals, N represents residues 93-131 of SEQ ID NO:2, 3, or 4, and C represents residues 142-156 of SEQ ID NO:2, 3, or 4. The presence or absence of polylysine or polyaspartate at the N-terminus and/or C-terminus thereof or the presence or absence of amidation at the C-terminus is as discussed above for the synthetic immunogenic but non-amyloidogenic peptide homologous to PrP. Exemplary sequences, which include both mono- and di-peptides of the homologous prion fragment, are set forth in SEQ ID NOS: 19-24 (homologs of human PrP) and 25-30 (homologs of bovine PrP).

Those of ordinary skill in the art will also appreciate that peptidomimetics of the synthetic immunogenic but non-deposit-forming polypeptide or peptide of the present invention, where the peptide bonds are replaced with non-peptide bonds, can also be used. Peptidomimetics can have various different structures (Ripka et al., Curr. Opin. Chem. Biol., 1998; 2:441-452). For example, peptidomimetics can be: (1) peptide analogues containing one or more amide bond replacements (Spatola, In: Chem. Biochem. Amino Acids, Pept., Proteins; Weinstein, B., Ed.; Marcel Dekker: New York, 1983; pp. 267-257); (2) peptide analogues with various conformational restrains (Hart and Rich, In: Pract. Med. Chem.; Wermuth, C., Ed., Acad. Press: London, U.K., 1996; pp. 393-412), (3) novel structures that replace the entire peptide backbone while retaining isosteric topography of the peptide (Farmer, In: Drug Design; Ariens, E. J., Ed.; Academic Press: New York, 1980; 10:119-143), and (4) various heterocyclic natural products or screening leads that mimic the function of the natural peptide (Fletcher and Campell, Chem. Rev., 1998; 98:763-795). Any suitable peptidomimetic can be used in the context of the present invention.

Mucosal Immunization

A number of strategies can be employed for oral immunization according to the invention, including the use of attenuated mutants of bacteria (i.e., *Salmonella* spp.) as carriers of antigens (Chabalgoity et al., Exp. Rev. Vaccines, 2002; 1:495-505; Mastroeni et al., Vet. J., 2001; 161:132-164; Cardenas and Clements, Clin. Microbiol. Rev., 1992; 5:328-342; Clements et al., 1992, In: Recombinant DNA Vaccines: Rationale and Strategy, Isaacson (ed.), Marcel Decker, New York. pp. 293-321; Clements and Cardenas, Res. Microbiol., 1990; 141:981-993; Clements and El-Morshidy, Infect. Immun., 1984; 46:564-569), encapsulation of antigens into microspheres composed of poly-DL-lactide-glycolide (PGL), protein-like polymers-proteinoids (Sanitago et al., Pharmaceutical Research, 1993; 10:1243-11247), gelatin capsules, different formulations of liposomes (Alving et al., Vaccine, 1986; 4:166-172; Garcon and Six, J. Immunol., 1993; 146: 3697-3702; Gould-Fogerite and Mannino, 1993, In: Liposome Technology 2nd Edition. Vol. III, Gregoriadis (ed.)), adsorption onto nanoparticles, use of lipophilic immune stimulating complexes (ISCOMS) (Mowat and Donachie, Immunology Today, 1991; 12:383-385), use of aluminum-based adjuvants such as aluminum hydroxide (Baylor, N W et al., Vaccine, 2002; 20 Suppl 3:S18-23 and addition of bacterial products with known adjuvant properties (Clements et al., Vaccine, 1988; 6:269-277; Elson, Immunology Today, 1989; 146:29-33; Lycke and Holmgren, Immunology, 1986; 59:301-308; Lycke et al., Eur. J. Immunol., 1992; 22:2277-2281). Bacterial products which can function as oral adjuvants include cholera toxin (CT), cholera toxin B (CTB) produced by various strains of *V. cholerae*, and the heat-labile enterotoxin (LT) produced by some enterotoxigenic strains of *Escherichia coli* (see, e.g. U.S. Pat. Nos. 6,440,423, 6,436, 407, and 6,019,982).

In preferred embodiments of the present invention, mucosal immunization to prion protein is achieved by administering (1) a prion protein with a cholera toxin adjuvant; (2) a prion protein conjugated to cholera toxin subunit B; or the combination of both; or (3) an attenuated *Salmonella* vector encoding a prion protein. These embodiments are described below.

Cholera enterotoxin (CT) as an adjuvant has been used in animals, and could thus be used, e.g., for chronic wasting disease vaccination. CT has also been proposed for human use (Tamura et al., Japanese Journal of Infectious Diseases, 2000; 53:98-106). CT is an 84,000 dalton polymeric protein composed of two major, non-covalently associated, immunologically distinct regions or domains ("cholera-A" and "cholera-B") (Finkelstein and LoSpalluto, J. Exp. Med., 1969; 130: 185-202). Orally administered CT does not induce tolerance against itself (Elson and Ealding, J. Immunol., 1984; 133: 2892-2897), but is a powerful adjuvant that augments the local (GI) and systemic serum antibody response via a Th-2 cell dependent pathway to co-administered antigens (Foss et al., Animal Health Research Reviews, 2000; 1:3-24; Fujihashi et al., Acta Odontologica Scandinavica, 2001; 59:301-308; Tamura et al., Japanese Journal of Infectious Diseases, 2000; 53:98-106; Czerkinsky et al., Proc. Natl. Acad. Sci. (USA), 1989; 57:1072-1077; Lycke and Holmgren, Immunology, 1986; 59:301-308). The Th-2 response is modulated by secretion of IL-4, IL-5, IL-6 and IL-10 which provide better help for B-cell responses, including those of IgG1, IgE and IgA isotypes in mice.

Use of cholera toxin in conjunction with prion protein allows for a strong humoral GI response, the site of entry of prions as well as a systemic humoral response, with little or no cytotoxic T-cell response. In one embodiment, a prion protein is administered in a mixture with CT. For example, heat aggregated CT has little toxicity but is a potent oral immunogen (Pierce et al., Infect. Immun., 1983; 40: 1112-1118). In one embodiment, CT (or LT) derivatives can be administered in a prion vaccine, orally or intranasally, as described by Tamura et al. (Japanese Journal of Infectious Diseases, 2000; 53:98-106), administering a single vaccine dose of around 5-500 µg, preferably about 100 µg of CT to an adult, in a volume of less than 0.5 ml.

In another embodiment, CT-B alone serves as an immunologic "carrier" (Cebra et al., 1986, In: Vaccines 86, Brown et al. (ed.), Cold Spring Harbor Laboratory, New York. p.p. 129-133; McKenzie and Halsey, J. Immunol., 1984; 133: 1818-1824) by conjugation to the prion protein. The amino acid sequence of CT-B is set forth in SEQ ID NO: 31. The B-subunit can be prepared by subjecting holotoxin to dissociation chromatography by gel filtration in the presence of a dissociating agent (i.e., guanidine HCl or formic acid). The isolated subunits are then pooled and the dissociating agent removed. Alternatively, the CT-B subunit can be produced by recombinant methods. The CT-B subunit is conjugated or crosslinked to the prion protein using known methods in the art for protein conjugation or cross-linking. See, e.g. Wong (Ed.), In: Chemistry of Protein Conjugation and Cross-Linking, CRC-Press, Boca Raton, Fl., 1991. According to a preferred embodiment, prion protein is linked to the CT-B subunit by reacting each substance with coupled to N-succinimidyl-(3-(2-pyridyl)-dithio)propionate (SPDP) (Pierce) at molar ratios of about 1:1 to about 1:20, preferably about 1:30, according to Czerkinsky et al., Proc. Natl. Acad. Sci. (USA), 1989; 57:1072-1077. SPDP reacts primarily with free amino groups in proteins (present e.g., on N-terminal residues and lysine residues), and introduces a reactive sulfydryl group that can form a di-sulfur bridge to another free sulfhydryl group on, e.g., another SPDP-modified protein. After separation from unreacted SPDP, a mixture of SPDP-rPrP and SPDP-CT-B is then reduced by adding a reducing agent such as DTT, producing a PrP-CT-B conjugate. Conjugation can also be achieved by reacting the prion or its fragments with CT and/or CT-B in the presence of glutaraldehyde. The prion protein or fragment is diluted to 1-20 mg/ml in 0.1M borate buffered saline (BBS) pH 7.4 and 100 mM glutaraldehyde (Sigma, St. Louis, Mo.) in BBS is added to a final concentration of 20 mM. The mixture is then incubated at room temperature for 6-30 hours under vigorous agitation. The reaction is stopped by quenching the mixture with 0.5 M glycine to a final concentration of 0.1M in glycine. A few minutes [about how many?] later the mixture is diluted tenfold with BBS and dialyzed against 2 mM BBS with several changes [about how many?] of the BBS, then lyophilized and kept at 4° C. until administered (McCarthy et al., J. Immunol. Methods, 1985; 82:349-358; McCarthy D. A. and Drake, A. F., Mol. Immunol., 1989; 26(9):875-881).

In another embodiment, a construct of rPrP with cholera toxin is produced by recombinantly expressing a protein where the CT-B subunit is already incorporated at the amino or carboxyl terminal, i.e., the fusion protein itself is recombinantly expressed. This may be advantageous in cases where the prion protein is insoluble or tend to aggregate, thus making post-translational modification difficult.

In another embodiment, E. coli heat-labile enterotoxin (LT) is used instead of the CT-B subunit. Also, mutants of LT have shown to be capable of successfully promoting a mucosal immune response or a mutant thereof produced by Escherichia coli (see, e.g., U.S. Pat. Nos. 6,440,423, 6,436, 407, and 6,019,982). Briefly, the mutant form of LT differs from the wild-type by a single amino acid substitution, Arg192Gly, rendering a trypsin sensitive site insensitive. The loss of the proteolytic site prevents the proteolytic processing of the A subunit into its toxic form, but the mutant retains the capability of enhancing an animal's immune response (e.g., IgG, IgA) to an antigen unrelated to LT with no toxic side effects. The LT or LT mutant can be administered together with PrP, or conjugated to PrP as described for CT-B.

In another embodiment, an attenuated strain of Salmonella typhimurium, preferably LVR01 (Chabalgoity et al., Vaccine, 2000; 19:460-469), LVR03 (a mouse-adapted derivative of LVR01), or SL3261 (Hoiseth et al., Nature, 1981; 291:238-239) or Salmonella typhi CVD908-htrA (Tacket et al., Infect Immun., 2000 March; 68(3): 1196-1201) or an attenuated Shigella strain, preferably WRSS1 (Kotloff et al., Infect. Immun., 2002; 70:2016-21) or Salmonella typhi Ty21a (VivoTif, Bema Beme, Clin Immunol 1999; 92:76-89 Switzerland), is used as a live vector containing the PrP cDNA to induce mucosal immunity to PrP. Salmonella vaccine strains have been extensively used in animal models to deliver foreign antigens and elicit a mucosal immune response (Lillard et al., Cellular and Molecular Biology, 2001; 47:1115-1120; Mastroeni et al., Veterinary Journal, 2001; 161:132-164; Pasetti et al., Clin. Immunol., 1999; 92:76-89; Levine et al., Journal of Biotechnology, 1996; 44:193-196) inducing a strong mucosal IgA and systemic IgG production against the foreign antigens delivered. This approach has also been successfully used in humans (Nardelli-Haeffiger et al., Infection and Immunity, 1996; 64:5219-5224; Tacket et al., Infection and Immunity, 1997; 65:452-456). In one embodiment, described for mouse PrP in Example 2, S. typhimurium LVR03 is transformed by electroporation with the PrP gene cloned in a plasmid under a bacterial promoter, and successful PrP expression verified by standard techniques. A vaccine can then be produced by preparing bacterial solutions of about $1 \times 10^{11}$ CFU/ml in sterile PBS.

In another embodiment, the immunogenicity of the prion vaccine of the present invention is increased by forming a conjugate between the prion protein and an immunostimulatory polymer molecule such as mannan (polymer of mannose), glucan (polymer of β1-2 glucose), tripalmitoyl-S-glycerine cysteine, and peptides which are currently approved for use in vaccines in humans. Such peptides, approved for use in vaccines, provide strong T-helper cell (Th) epitopes from potent immunogens such as tetanus toxin, pertussis toxin, the measles virus F protein, and the hepatitis B virus surface antigen (HBsAg), as disclosed in U.S. Pat. No. 5,843,446, which is hereby incorporated by reference. The Th epitopes selected to be conjugated to the synthetic peptide are preferably capable of eliciting T helper cell responses in large numbers of individuals expressing diverse MHC haplotypes. These epitopes function in many different individuals of a heterogeneous population and are considered to be promiscuous Th epitopes. Promiscuous Th epitopes provide an advantage of eliciting potent antibody responses in most members of genetically diverse population groups.

The T-helper cell epitopes conjugated/cross-linked to the prion protein of the present invention are also advantageously selected not only for a capacity to cause immune responses in most members of a given population, but also for a capacity to cause memory/recall responses. When the mammal is human, the vast majority of human subjects/patients receiving immunotherapy with the prion vaccine of the present invention will most likely already have been immunized with the pediatric vaccines (i.e., measles+mumps+rubella and diphtheria+pertussis+tetanus vaccines) and, possibly, the hepatitis B virus vaccine. These patients have therefore been previously exposed to at least one of the Th epitopes present in pediatric vaccines. Prior exposure to a Th epitope through immunization with the standard vaccines should establish Th cell clones which can immediately proliferate upon administration of the synthetic peptide (i.e., a recall response), thereby stimulating rapid B cell responses to prion peptides and deposits.

While the Th epitopes that may be used in the conjugate with the prion protein of the invention are promiscuous, they are not universal. This characteristic means that the Th epitopes are reactive in a large segment of an outbred population expressing different MHC antigens (reactive in 50 to 90% of the population), but not in all members of that population. To provide a comprehensive, approaching universal, immune reactivity for the prion vaccine according to the present invention, a mixture of conjugates with different Th epitopes cross-linked to a prion protein can be prepared. For example, a combination of four conjugates with promiscuous Th epitopes from tetanus and pertussis toxins, measles virus F protein and HBsAg may be effective.

The Th epitopes in the immunostimulatory peptide cross-linked to the synthetic non-deposit-forming peptide according to the present invention include hepatitis B surface antigen T helper cell epitopes, pertussis toxin T helper cell epitopes, tetanus toxin T helper cell epitopes, measles virus F protein T helper cell epitope, *Chlamydia trachomitis* major outer membrane protein T helper cell epitopes, diphtheria toxin T helper cell epitopes, *Plasmodium falciparum* circumsporozoite T helper cell epitopes, *Schistosoma mansoni* triose phosphate isomerase T helper cell epitopes, *Escherichia coli* TraT T helper cell epitopes and are disclosed in U.S. Pat. No. 5,843,446, the entire disclosure of which is incorporated herein by reference.

Extrinsic adjuvants can also provoke a potent mucosal immune responses to antigens. These include liposomes.

Vaccine Formulation

The immunizing compositions of the present invention comprise an immunoeffective amount of one or more prion proteins or peptides; at least one adjuvant, which may or may not be conjugated to or express a prion protein; and a pharmaceutically acceptable carrier. Such compositions in dosage unit form can contain about 0.5 μg to about 1 mg of each prion protein or conjugate per kg body weight. When delivered in multiple doses, the dosage unit form is conveniently divided into the appropriate amounts per dosage. The vaccine may also include a pharmaceutically acceptable carrier, excipient, diluent, or auxiliary agent. Such formulations are readily determined by one of ordinary skill in the art and include formulations for immediate release and for sustained release, e.g., microencapsulation.

Immunizing compositions which contain cocktails of two or more prion proteins or conjugates enhance immunoefficacy in a broader population and thus provide a better immune response to prion proteins and prion deposits. Other immunostimulatory synthetic polypeptide/peptide immunogens are arrived at through modification into lipopeptides so as to provide built-in adjuvanticity for potent vaccines. The immune response to prion immunogens of the present invention can be improved by delivery through entrapment in or on biodegradable microparticles of the type described by O'Hagan et al. (Immunology 1991; 73:239-42). The immunogens can be encapsulated with an adjuvant. Alternatively, immunogens may be formulated separately from adjuvant, and the microparticles administered with an immunostimulatory adjuvant as described herein.

Microparticles may provide improved efficacy by potentiating immune responses to an immunogen and to provide time-controlled release for sustained or periodic responses, for mucosal administration (O'Hagan et al., Immunology 1991; 73:239-42). Thus, a prion protein or prion protein-conjugate in microparticulate form can be mixed with exogenous adjuvant/emulsion formulations. For example, the absorbable suture material poly(lactide-co-glycolide) co-polymer can be fashioned into microparticles containing immunogen. Following oral or parenteral administration, microparticle hydrolysis in vivo produces the non-toxic byproducts, lactic and glycolic acids, and releases immunogen largely unaltered by the entrapment process. The rate of microparticle degradation and the release of entrapped immunogen can be controlled by several parameters, which include (1) the ratio of polymers used in particle formation (particles with higher co-glycolide concentrations degrade more rapidly); (2) particle size, (smaller particles degrade more rapidly than larger ones); and, (3) entrapment efficiency, (particles with higher concentrations of entrapped antigen degrade more rapidly than particles with lower loads). Microparticle formulations can also provide primary and subsequent booster immunizations in a single administration by mixing immunogen entrapped microparticles with different release rates. Single dose formulations capable of releasing antigen ranging from less than one week to greater than six months can be readily achieved.

The vaccine compositions described herein can be prepared by methods known per se for the preparation of pharmaceutically acceptable compositions which can be administered to subjects (for example, see Remington's Pharmaceutical Sciences (Mack Publishing Company, Easton, Pa., USA 1985)). The composition can be a liquid solution, suspension, emulsion, tablet, pill, capsule, sustained release formulation, or powder. For oral administration, the vaccine can take the form of, for example, tablets or capsules prepared by conventional means with pharmaceutically acceptable excipients such as binding agents (e.g., pregelatinized maize starch, polyvinyl-pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art.

Preparations for oral administration can take the form of, for example, solutions, syrups, emulsions or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

After pharmaceutical compositions have been prepared, they can be placed in an appropriate container and labeled for treatment of an indicated condition. Such labeling would include amount, frequency, and method of administration.

Vaccine Testing

Adjuvants that stimulate mucosal immunity and/or a Th-2 response are used. These can be distinguished from other types of adjuvants by various modes of testing known in the art, including in vivo and in vitro assays.

For example, a mucosal immune response is characterized by elevated levels of IgA or IgG in the gut. An adjuvant which, when mucosally administered together with a prion protein, result in at least a three-fold, preferably a 4-fold, and most preferably a 5-fold increase in the levels of IgA, IgG, or both IgA and IgG, in the gut region of a patient or experimental animal, is an adjuvant capable of eliciting a humoral immune response according to the invention. Suitable assays are described in Mastroeni et al., (Vet J 2001; 161:132-164), and references cited therein.

Other in vivo assays are those that evaluate or pre-clinically optimize prion vaccines in eliciting a mucosal immune response preventing, delaying, or reducing the formation of the aggregates, deposits, or fibrils involving the peptides associated with prionoses, in an experimental animal model. The animal studies can be designed to evaluate preventive or prophylactic vaccination (i.e., vaccine administration before any symptom of disease) or treatment of an already existing condition (i.e., vaccine administration after a disease symptom). Preferred, although nonlimiting, animal models are transgenic or non-transgenic mice and rats, as well as monkeys, dogs, cats, sheep and cattle. Preferably, the animals develop a conformational disease spontaneously, or the development of a conformational disease can be triggered, i.e., by administration of a disease agent (e.g., scrapie to induce prion disease).

A successful vaccine primarily elicits a Th-2 response, and preferably, although not necessarily, avoids strong cytotoxic T-lymphocyte (CTL) responses, the most prominent feature of the Th-1 response. The Th-2 response is an acquired immune response whose most prominent feature is high antibody production relative to the amount of cytotoxic T lymphocyte activity. The Th-1 response is promoted by $CD4^+$ Th-1 T-helper cells, while the Th-2 response is promoted by $CD4^+$ Th-2 T-helper cells. Testing of the relative degrees of Th-1 versus Th-2 type response can be conducted as described in Examples 1 and 2. For example, cytokine production and proliferation of $CD4^+$ T-cells isolated from spleen and Peyer's patches in response to immunogen is measured and compared to a control. Cytokine levels are determined in the supernatants as described (Lillard et al., Cellular and Molecular Biology, 2001; 47:1115-1120), and proliferation can be determined by adding a detectable (e.g., radiolabeled) nucleotide which is incorporated into the DNA of proliferating cells. A high level of Interleukin-4 (IL-4), IL-5, IL-6 and IL-10 in the media and a high B-cell proliferation rate would indicate a successful Th-2 response. Conversely, a low level of IL-2, Interferon-γ, and tumor necrosis factor-beta would indicate a low or moderate Th-1 response.

Several animal models have been established for the study of conformational diseases and their progression. For example, the Examples describe the use of a CD-1 mouse model, which is a strain of a wild-type mouse, for investigating the delay of onset of prion disease when administering a recombinant prion peptide or anti-prion antibodies before or after injection of scrapie-infected mouse brain tissue. In this model, a preparation of prion proteins or peptides can be administered either before exposure to scrapie for the study of mucosal immunization, after exposure to scrapie but before onset of prion disease to study prophylactic capabilities (i.e., to delay onset of disease), and after the onset of prion disease to evaluate treatment potential. Several other mouse strains that are useful for the study of prion disease are known in the art.

Specific protocols for each type of peptide or antibody preparation and disease type can be designed using no more than routine experimentation combined with general knowledge in the art and the present disclosure. Typical vaccination protocols are also provided in Sigurdsson et al. (Am J Pathol 2001; 159:439-447 and 2002; 161:13-17), and the type of adjuvant and dosages can be varied or optimized as appropriate.

Assessment of vaccination efficacy is conducted using standard methods such as histological examination using, for example, examination of sectioned tissues of interest, antibody staining techniques to visualize the extent of deposits or fibrils in selected tissues, ELISA methods for estimating plasma or tissue concentrations of the disease-associated peptide or endogenous antibodies directed to the disease-associated peptide, or testing whether deposits or aggregates of the disease-associated peptide are resistant to proteinase digestion.

Vaccine efficacy in preventing or delaying a neurodegenerative conformational disorder can also be evaluated by testing for motor coordination and/or cognitive capabilities at appropriate intervals during disease progression. For example, locomotor activity of a vaccinated or control animal can be tested by putting the animal; typically a rodent, into a closed activity box for 5 minutes. The animal's activity in the box is detected by photoreceptors in the box, so that whenever an animal crosses the receptor, an activity count is recorded. The activity box can record activity counts per minute. See, also, Sobotka et al., Pharmacology, 1978; 16:287-94. Alternatively, the ability of the animal to cross a traverse beam can be evaluated. The animal is given 1 unscored training trial, preventing injury from falling by placing a soft cover underneath the beam. An animal that falls off is placed back into the position they maintained prior to the fall. After training, each animal is tested twice. Errors are defined as footslips and recorded both numerically and using Feeney scores. See, also, Quartermain et al., Neurosci. Lett., 2000; 288:155-8. Motor coordination can also be studied using a rotarod. The animal is placed onto a clean rod (diameter 3.6 cm) for 30 seconds. With each 30-sec interval, the rotation speed is increased incrementally. Total time (including the 30-sec on the quiescent rod) and RPM when the animal falls down is recorded. A soft cover is placed beneath the apparatus to prevent potential injury from falling. Each animal is tested thrice with an intertrial interval of fifteen minutes. See, also, Quartermain et al., Neurosci. Lett., 2000; 288:155-8. An alternative test is observing the activity level and competency of the mice on an apparatus containing a series of parallel bars (3 mm in diameter) placed 7 mm apart. The initial clinical findings are a reduction in activity and/or the ability of the mice to traverse the parallel bars. This clinical endpoint correlates with the pathological development of CNS scrapie infection (Sigurdsson et al, Am J Pathol 2002 161: 13-17; Neurosci Lett 2003 336: 185-187).

As for cognitive tests, animals can be randomly split into equivalent groups and then run on a series of cognitive tests such all groups receive each test in a different sequential order. Cognitive testing can be made in various settings known in the art, e.g., radial arm mazes, linear mazes, water mazes, and goal boxes. For example, in a maze experiment, each animal can undergo a predetermined time of adaptation, consisting of 15 minutes free moving in the maze, with pieces of fruit loops in each (open) arm of the maze. Subjects are then exposed to doors. Animals are food deprived before the first adaptation with, for example, approximately ten percent body weight loss. Fruit loops are added to normal diet before deprivation schedule starts. Testing include recording correct and incorrect arms entered. Animals are placed in the center of the maze and all doors are opened. After entry into an arm, the animal must find and eat the reinforcer before the door is opened to re-enter the center of the maze. Testing ends when all arms are entered and reinforcers found. Re-entry into an arm constitutes an error. Total number of errors and time to enter all arms are recorded. Access to food is given for 3-4 hours (depending on age, body weight loss) daily. Radial arms mazes and other types of cognitive tests are described in Ammassari-Teule et al., Behav. Brain Res., 1985; 17:9-16; Roullet et al., Physiol. Behav., 1998; 64:203-7; and Roullet et al., Physiol. Behav., 1995; 58:1189-95.

Administration

Immunotherapy regimens which produce distinct and detectable immune responses following the administration of the fewest number of doses, ideally only one dose, are employed. Specific administration schedules and dosages for the prion vaccine can be readily determined by the ordinary skilled artisan. The immunization protocol is designed to primarily induce mucosal immunity to the prion protein. The vaccine can be administered in solid form for oral administration or in liquid form. Liquid forms may be administered to a subject either orally or intranasally. For example, unit dosage forms can be administered in intranasal form via topical use of suitable intranasal vehicles.

For example, the vaccines can be mucosally administered as a single dose or divided into multiple doses for administration. In one embodiment, vaccine is administered at least three times at spaced apart intervals, e.g., once weekly, once every 10 days, and once every two weeks. In another embodiment, a single vaccine dose is administered at day 0, and a booster vaccine administered about one week, two weeks, one month, or 2 months later.

For administration to wild animals such as deer or elk, the vaccine can be mixed with food, and the food placed in a suitable container in an area where the target population lives using bait and baiting systems as have been developed for free-ranging animals for delivery of oral rabies vaccine (where the vaccine is mixed with food the animal likes to eat. (Knobel et al., J. Wildl. Dis., 2002; 38:352-62).

EXAMPLES

The following Example(s) are understood to be exemplary only, and do not limit the scope of the invention Example 1

Active Immunization with Cholera Toxin B Subunit as Adjuvant

This example describes the use of a conjugate of recombinant PrP (rPrP) and cholera toxin B subunit as a vaccine to induce mucosal immunity to prion protein in CD-1 mice. Vaccinated mice are then exposed orally to either 139A or ME7 $PrP^{Sc}$, which are both strains of scrapie (Carp and Rubenstein, Semin. Virol 1991; 2:203-213; Kascsak et al., J Virol, 1986; 59: 676-683).

Cholera toxin (CT) and Cholera toxin B subunit (CTB) (Sigma) are used. The CTB and rPrP are each coupled to N-succinimidyl-(3-(2-pyridyl)-dithio)propionate (SPDP) (Pierce) at molar ratios of 1:30, using a previously published protocol (Czerkinsky et al., Proc. Natl. Acad. Sci. (USA), 1989; 57:1072-1077). The preparations are freed of unreacted SPDP by gel filtration through Sephadex G25 columns (Pierce) or dialysis. The rPrP is then reduced for 20 min at room temperature with 50 mM dithiothreitol in 0.1M sodium acetate buffer-0.1M NaCl (pH 4.5) and gel filtered through a Sephadex G25 column equilibrated with 0.1M sodium phosphate buffer-0.1M NaCl (pH 7.5) or dialyzed against the same buffer; then mixed with the CTB for 30 minutes and the coupled material passed trough a G25 column or dialyzed against PBS.

Groups of 20 CD-1 2-month old female mice are exposed to the immunogens by intragastric intubation. The immunogens are diluted in 0.35M $NaHCO_3$ and 0.5 ml of the solutions are introduced containing: 15 μg of CTB, 5 μg of CT, 20 μg of rPrP-CTB conjugate with or without free CT (5 μg) as adjuvant; 20 μg of PrP89-143-CTB (amino acids 89 to 143 of the mouse prion protein linked to CTB) with or without 5 μg CT, 20 μg of rPrP-CTB conjugate with 30 μg of free CTB; and 150 μg of rPrP (unconjugated) with or without 5 μg of CT. Immunization is performed on days 0, 10 and 20, similar to past protocols (Czerkinsky et al., Proc. Natl. Acad. Sci. (USA), 1989; 57:1072-1077). Eight weeks following the first vaccination, the mice are bled and the anti-rPrP IgG and IgA antibody titers are determined by ELISA.

Selected animals are also sacrificed in each group to allow for analysis of antibody-producing cells. These studies provide information on the specific proliferative responses and the degree of Th-1 versus Th-2 type cytokine production. A high Th-2 response and a low-Th-1 response would indicate that a strong humoral antibody response had been elicited against prion disease, while minimizing a potentially toxic T-cell response. Single cell suspensions of spleen and Peyer's patches are prepared by aseptically removing tissue and passage through nylon mesh. Cells are washed in RPMI 1640. Lymphocytes are maintained in complete media, consisting of RPMI 1641 supplemented with 10 ml/l of nonessential amino acids (Gibco), 1 mM sodium pyruvate (Sigma), 10 mM HEPES, 100 units/ml penicillin, 100 μg/ml streptomycin, 40 μg/ml gentamycin, 50 μM mercaptoethanol and 10% fetal bovine serum. The purified CD4+ T-cells from immunized mice are cultured at a density of $5\times10^6$ cell/ml with $1\times10^6$ cells/ml of T-cell depleted and irradiated splenic feeder cells in complete medium containing 1 μg/ml rPrP (Aucouturier et al., J. Clin. Invest., 2001; 108:703-708, Lillard et al., Cellular and Molecular Biology, 2001). Purified T-cells from unimmunized mice are stimulated with anti-CD2 monoclonal antibody (Pharmingen) or rPrP as a positive and negative control, respectively. To determine immunogen specific proliferation responses, purified CD4+ T-cells are cultured in 96 well round-bottom plates. Following incubation for 3 days cells are pulsed with 0.5 μCi of methyl-3H-thymidine (Amersham) per well for 18 hr. Cells are harvested on glass microfiber filter paper and radioactivity levels are obtained by liquid scintillation counting. In addition, 2 ml of culture supernatants from 12 well flat-bottom plates will be harvested after 5 days of incubation. Cytokine levels are determined in the supernatants as described in Lillard et al. (Cellular and Molecular Biology, 2001; 47:1115-1120), hereby incorporated by reference in its entirety. An at least 5-fold increase in the levels of cytokines such as IL-4, IL-5, IL-6 and/or IL-10 indicate a successful mucosal immune response, while levels less than 1.5 of the baseline of IL-2, IF-γ and TNF-β are indicative of the absence of a sufficient Th-1 response.

The mice are subsequently divided into two groups matched for their titer to PrPSc and are inoculated by intragastric intubation with a brain homogenate of the mouse-adapted scrapie strain ME7 or 139A at a 1-fold and a 10 fold dilution. The mice are then subjected to weekly behavioral testing for motor-coordination to evaluate clinical symptoms of prion disease. Briefly, the activity level and competency of the mice on an apparatus containing a series of parallel bars (3 mm in diameter) placed 7 mm apart is observed. The initial clinical findings are a reduction in activity and/or the ability of the mice to traverse the parallel bars. This clinical endpoint correlates with the pathological development of CNS scrapie infection (Sigurdsson et al., Am J Pathol, 2002; 161:13-17; Aucouturier et al., J Clin Invest, 2001; 108:703-708; Sigurdsson et al., TIMM, 2002; 8:411-413). At the time of sacrifice (after the mice score positive for scrapie for 3 weeks or at 300 days if mice do not get ill) serum antibody levels to rPrP, $PrP^C}$ and $PrP^{Sc}$ are determined, as well as proliferation responses of cells from Peyer's patches and spleen. The amounts of spongiform change in the brains by histology and the levels of $PrP^{Sc}$ by Western blotting are also determined.

Example 2

Active Immunization with *S. typhimurium* Vaccine Strain as Vector

In this example, mucosal immunity to PrP is induced by use of *Salmonella typhimurium* vaccine strains as a vector containing the mouse PrP cDNA (Table 1).

Mouse adapted *S. typhimurium* strain LVR03 is used. *S. typhimurium* LVR03 is transformed by electroporation with a plasmid encoding the PrP gene under a bacterial promoter in 10% glycerol-water using a GenePulser (Bio-Rad). The expression of rPrP by the *S. typhimurium* strain is assessed by SDS-PAGE and Western blotting. The bacteria are maintained on Luria-agar tubes at room temperature or as frozen cultures at −80° C. For vaccine preparation, bacteria are grown from the stock in tubes containing 2 ml of Luria broth (LB) 25 g/L with the addition of 50 μg/ml of ampicillin; then incubated at 37° C., on a shaker, overnight. Then, 50 μl are transferred to new tubes containing 2 ml of LB with ampicillin (LB-amp) liquid, incubated on a shaker for 8 hours at 37° C. and then transferred, one or two tubes per 300 ml of LB-amp, into two liter flasks, depending on the growth rate of each preparation. The flasks are incubated overnight on a shaker at 37° C., then centrifuged in 50 ml tubes for 20 minutes at 1500×g; washed with sterile PBS, centrifuged and resuspended in the appropriate delivery liquid. The bacterial suspensions are diluted to an optical density of 0.5 at 600 nm of 0.5 (equivalent to $5\times10^{8}$ CFU/ml and concentrated to $1\times10^{11}$ CFU/ml by centrifugation and re-suspension in an appropriate volume of sterile PBS.

CD-1 mice are immunized via gastric tube, following overnight fasting, with approximately $2\times10^{9}$ CFU of vaccine strain diluted in 0.35M $NaHCO_3$ in a 0.5 ml volume. Mice are boosted in an identical manner 7 days, 21 days and/or 30 days later. Control mice receive the vaccine strain without the rPrP plasmid. Prior to and eight weeks following the first vaccination, the mice are bled and the anti-rPrP IgG and IgA antibody titers are determined by ELISA using previously published methods (see, e.g., Sigurdsson et al., Am J Pathol 2001; 159:439-447 and Am J Pathol 2002; 161:13-17). The same measurements are performed using mouse feces. At least 6 feces pellets are collected from each mouse and transferred immediately to 10 mM PBS containing 0.5% sodium dodecyl sulfate and 1 mM PMSF. The pellets are then disintegrated with a spatula, vortexed for at least 30 seconds, centrifuged at 14,000 rpm (20, 817 g) for 25 minutes and the supernatant is then separated and kept at −20° C. until analyzed.

The mice are subsequently divided into two groups matched for their titer to PrPSc and are inoculated by intragastric intubation with a brain homogenate of the mouse-adapted scrapie strain ME7 or 139A at a 1-fold and a 10-fold dilution. The mice are then subjected to weekly behavioral testing, as described in Example 1.

At the time of sacrifice (after the mice score positive for scrapie for 3 weeks or at 300 days if mice do not get ill) serum antibody levels to recPrP, $PrP^{c}$ and $PrP^{Sc}$ are determined, as well as T-cell proliferation responses of cells from the Peyer's patches and spleen, as described above. The amounts of spongiform change in the brains by histology and the levels of PrPSc by Western blotting are also determined.

Example 3

Mucosal Vaccination

This example describes the comparison and optimization of mucosal immunization protocols in peripherally infected prion model mice. The following vaccines and controls are tested, using 10 mice in each test group (CT=cholera toxin; CTB=cholera toxin subunit B): recPrP, CTB, PrP89-143, CTB-PrP89-143, CTB-recPrP, CTB-recPrP+CT, CTB-PrP89-143+CT, *salmonella* vector, *salmonella* LVR01+PrP, and controls.

Mice have the active vaccine introduced by gastric lavage at 6 weeks of age. Mice are deprived of food for at least 8 hours prior to administration of vaccine and are not fed again until at least 6 hours following the vaccination. These steps are repeated at 1 or 2 week intervals for additional 1 or 2 doses. At 6 weeks the mice are bled. The mice are also bled mid-way through the experiment (at about day 60) and at the time of sacrifice (after they have been determined to be clinically ill on 3 separate occasions or if they never show signs of illness at day 300). The mice are briefly restrained in a tail access rodent restrainer (Stoelting, Cat. #51338) and tail blood collected in heparinized microcapillary tubes (1-2 tubes per mouse; per bleeding; 40-60 μl).

Both prion strains 139A and ME7 are used for inoculation in separate groups of animals. The two different prion strains are used because prion behavior is greatly affected by strain differences. 139A and ME7 are chosen since they have very different biophysical properties. 139A is relatively proteinase K (PK) sensitive, while ME7 is highly PK resistant. In order to be able to generalize to humans, it is important to test in animal studies that similar findings are achieved in at least two different animal strains of prions. The experiments are also done with scrapie inoculation at two different dilutions (1:2 and 1:10). This is standard procedure for prion infection experiments and is required to determine if the effect seen is specific or not.

Thus, following the $3^{rd}$ vaccination, mice are inoculated with either 139A or ME7 strain mouse prions by an intraperitoneal injection of 100 μl 10% brain homogenate in phosphate buffer saline (prepared from a mouse with clinical infection with the respective strain of prion). Mice are then observed weekly for the development of scrapie infection using a well characterized behavior test of co-ordination. The typical incubation period for both strains is about 130-150 days. The analysis of clinical symptoms consists of observing the activity level and competency of the mice on an apparatus containing a series of parallel bars (3 mm in diameter) placed 7 mm apart. The initial clinical findings are a reduction in activity and/or a reduced ability of the mice to traverse the parallel bars. Once the mice score positive on 3 separate occasions by an observer blinded to their experimental status, the mice are sacrificed by an overdose (i.p.) of anesthetic (100 mg/kg sodium pentobarbital). Their brains are processed for histology and Western blots. Mice which never score sick are observed until 300 days, at which point they are euthanized by an overdose (i.p.) of anesthetic (100 mg/kg sodium pentobarbital). Their brains are also processed for histology and Western blots.

Example 4

Update on Active Immunization Studies Using Mucosal PrP Vaccine

Figure 1B:
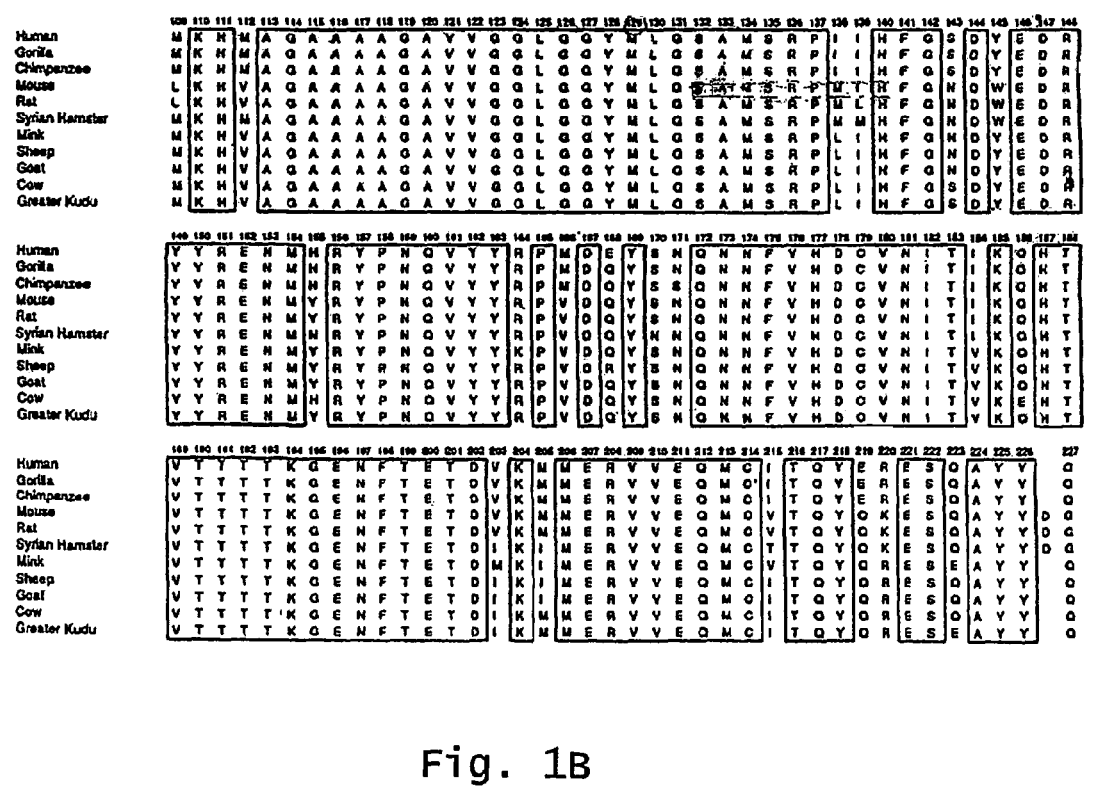

This Example describes immunization of mice using a mucosal vaccine of *Salmonella* LVR01 vaccine strain. The mice were inoculated orally with 139A PrP$^{Sc}$, and have been followed for 350 days post-inoculation (FIG. 1).

Plasmids containing one copy of PrP gene (PrP×1) or two tandem copies (PrP×2) were constructed as previously described (Chalagoity et al., Mol Microb., 1996; 19(4):791-801). *Salmonella* LVR01 vaccine strain was transformed with these plasmids or with the parental plasmid without Prp. Groups of 20 mice were orally inoculated with: LVR01-PrP×2 (PrP×2 group), LVR01-PrP×1 (PrP×1 group) or LVR01 without PrP (control-sham). Twenty mice were not inoculated with LVR01 (control). Animals each received $1$–$2 \times 10^{10}$ cells of LVR01 in PBS. Oral inoculation was repeated after 1 week. Six weeks later, all 80 animals were orally infected with a 10% brain homogenate of 139A PrP$^{Sc}$. Following scrapie inoculation, the mice were monitored for clinical signs of scrapie, starting a few weeks before the expected onset of symptoms.

FIG. 2 shows a Kaplan and Meier survival curve after 350 days. 60% of the inoculated mice with the vaccine expressing either one or two copies of PrP are alive and well. Between 90 and 80% of the controls are dead from prion infection. This difference between the groups (PrP expressing versus controls) is highly statistically significant (p=0.0007).

Figure 3:
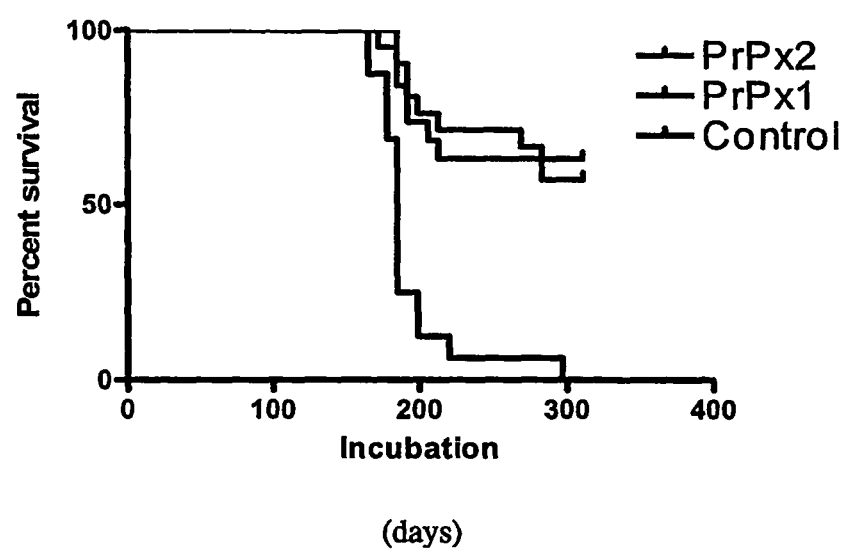
FIG. 3 shows a Kaplan-Meier survival curve for mice orally inoculated with PrP×2, PrP×1 or control. These inoculations were administered with $NaHCO_3$, pH 8.3, mixed with aluminum hydroxide (4:1; v/v).

This experiment was repeated in a second set of 60 CD-1 mice. Groups of 20 mice each were orally inoculated with: LVR01-PrP×2 (PrP×2 group), LVR01-PrP×1 (PrP×1 group) or LVR01 without PrP (control-sham). The method was slightly different in that the LVR01 was orally inoculated with NaHCO$_3$, pH 8.3, mixed with aluminum hydroxide (4:1; v/v) in order to increase the survival of the *Salmonella* in the low pH environment of the stomach, and in that the gastric inoculation procedure had been improved to reduce vomiting etc. The results from this experiment are shown in FIG. 3.

The difference between either PrP×2 or PrP×1 versus the control group is highly statistically significant (p<0.0001). There were no evident side-effects in the vaccinated animals. These two experiments show that the mucosal vaccine is effective in the majority of orally exposed mice, and that this effect is reproducible. This approach can be translated very easily to an oral vaccine for use in deer or cattle, and has the potential for human use with further development.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

SEQUENCE LISTING

<160> NUMBER OF SEQ ID NOS: 32

<210> SEQ ID NO 1
<211> LENGTH: 253
<212> TYPE: PRT
<213> ORGANISM: Homo sapiens

<400> SEQUENCE: 1

```
Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140
```

```
Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
                195                 200                 205

Val Val Glu Gln Met Cys Ile Thr Gln Tyr Glu Arg Glu Ser Gln Ala
            210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 2
<211> LENGTH: 264
<212> TYPE: PRT
<213> ORGANISM: Bovine

<400> SEQUENCE: 2

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
                20                  25                  30

Gly Trp Asn Thr Gly Gly Ser Arg Tyr Pro Gly Gln Gly Ser Pro Gly
                35                  40                  45

Gly Asn Arg Tyr Pro Pro Gln Gly Gly Gly Trp Gly Gln Pro His
50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
                85                  90                  95

Gly Gly Gly Gly Trp Gly Gln Gly Gly Thr His Gly Gln Trp Asn Lys
                100                 105                 110

Pro Ser Lys Pro Lys Thr Asn Met Lys His Val Ala Gly Ala Ala Ala
                115                 120                 125

Ala Gly Ala Val Val Gly Gly Leu Gly Gly Tyr Met Leu Gly Ser Ala
            130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
                180                 185                 190

Ile Thr Val Lys Glu His Thr Val Thr Thr Thr Thr Lys Gly Glu Asn
                195                 200                 205

Phe Thr Glu Thr Asp Ile Lys Met Met Glu Arg Val Val Glu Gln Met
            210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
                260
```

<210> SEQ ID NO 3
<211> LENGTH: 256
<212> TYPE: PRT
<213> ORGANISM: Deer

<400> SEQUENCE: 3

```
Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255
```

<210> SEQ ID NO 4
<211> LENGTH: 256
<212> TYPE: PRT
<213> ORGANISM: Elk

<400> SEQUENCE: 4

```
Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Gly Trp Gly Gln Gly
```

```
            85                  90                  95
Gly Thr His Ser Gln Trp Asn Lys Pro Ser Lys Pro Lys Thr Asn Met
            100                 105                 110
Lys His Val Ala Gly Ala Ala Ala Gly Ala Val Val Gly Gly Leu
            115                 120                 125
Gly Gly Tyr Met Leu Gly Ser Ala Met Ser Arg Pro Leu Ile His Phe
            130                 135                 140
Gly Asn Asp Tyr Glu Asp Arg Tyr Tyr Arg Glu Asn Met Tyr Arg Tyr
145                 150                 155                 160
Pro Asn Gln Val Tyr Tyr Arg Pro Val Asp Gln Tyr Asn Asn Gln Asn
                165                 170                 175
Thr Phe Val His Asp Cys Val Asn Ile Thr Val Lys Gln His Thr Val
            180                 185                 190
Thr Thr Thr Thr Lys Gly Glu Asn Phe Thr Glu Thr Asp Ile Lys Met
            195                 200                 205
Met Glu Arg Val Val Glu Gln Met Cys Ile Thr Gln Tyr Gln Arg Glu
            210                 215                 220
Ser Glu Ala Tyr Tyr Gln Arg Gly Ala Ser Val Ile Leu Phe Ser Ser
225                 230                 235                 240
Pro Pro Val Ile Leu Leu Ile Ser Phe Leu Ile Phe Leu Ile Val Gly
                245                 250                 255

<210> SEQ ID NO 5
<211> LENGTH: 256
<212> TYPE: PRT
<213> ORGANISM: Odocoileus hemionus

<400> SEQUENCE: 5

Met Val Lys Ser His Ile Gly Ser Trp Ile Leu Val Leu Phe Val Ala
1               5                   10                  15
Met Trp Ser Asp Val Gly Leu Cys Lys Lys Arg Pro Lys Pro Gly Gly
            20                  25                  30
Gly Trp Asn Thr Gly Gly Ser Arg Tyr Pro Gly Gln Gly Ser Pro Gly
            35                  40                  45
Gly Asn Arg Tyr Pro Pro Gln Gly Gly Gly Trp Gly Gln Pro His
50                  55                  60
Gly Gly Gly Trp Gly Gln Pro His Gly Gly Trp Gly Gln Pro His
65                  70                  75                  80
Gly Gly Gly Trp Gly Gln Pro His Gly Gly Gly Trp Gly Gln Gly
            85                  90                  95
Gly Thr His Ser Gln Trp Asn Lys Pro Ser Lys Pro Lys Thr Asn Met
            100                 105                 110
Lys His Val Ala Gly Ala Ala Ala Gly Ala Val Val Gly Gly Leu
            115                 120                 125
Gly Gly Tyr Met Leu Gly Ser Ala Met Asn Arg Pro Leu Ile His Phe
            130                 135                 140
Gly Asn Asp Tyr Glu Asp Arg Tyr Tyr Arg Glu Asn Met Tyr Arg Tyr
145                 150                 155                 160
Pro Asn Gln Val Tyr Tyr Arg Pro Val Asp Gln Tyr Asn Asn Gln Asn
                165                 170                 175
Thr Phe Val His Asp Cys Val Asn Ile Thr Val Lys Gln His Thr Val
            180                 185                 190
Thr Thr Thr Thr Lys Gly Glu Asn Phe Thr Glu Thr Asp Ile Lys Met
            195                 200                 205
Met Glu Arg Val Val Glu Gln Met Cys Ile Thr Gln Tyr Gln Arg Glu
```

```
                  210                 215                 220
Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 6
<211> LENGTH: 254
<212> TYPE: PRT
<213> ORGANISM: Mus musculus

<400> SEQUENCE: 6

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Thr Trp Gly Gln Pro His Gly Gly Gly Trp
        50                  55                  60

Gly Gln Pro His Gly Gly Ser Trp Gly Gln Pro Gly Gly Gly Ser Trp
65                  70                  75                  80

Gly Gln Pro His Gly Gly Trp Gly Gln Gly Gly Thr His Asn
                85                  90                  95

Gln Trp Asn Lys Pro Ser Lys Pro Lys Thr Asn Leu Lys His Val Ala
                100                 105                 110

Gly Ala Ala Ala Gly Ala Val Val Gly Gly Leu Gly Gly Tyr Met
            115                 120                 125

Leu Gly Ser Ala Met Ser Arg Pro Met Ile His Phe Gly Asn Asp Trp
        130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
                180                 185                 190

Lys Gly Glu Asn Phe Thr Glu Thr Asp Val Lys Met Met Glu Arg Val
            195                 200                 205

Val Glu Gln Met Cys Val Thr Gln Tyr Gln Lys Glu Ser Asp Ala Tyr
        210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 7
<211> LENGTH: 225
<212> TYPE: PRT
<213> ORGANISM: Rattus norvegicus

<400> SEQUENCE: 7

Gly Gly Trp Asn Thr Gly Gly Ser Arg Tyr Pro Gly Gln Gly Ser Pro
1               5                   10                  15

Gly Gly Asn Arg Tyr Pro Pro Gln Ser Gly Gly Thr Trp Gly Gln Pro
                20                  25                  30

His Gly Gly Gly Trp Gly Gln Pro His Gly Gly Trp Gly Gln Pro
            35                  40                  45
```

-continued

His Gly Gly Gly Trp Gly Gln Pro His Gly Gly Trp Ser Gln Gly
        50                  55                  60

Gly Gly Thr His Asn Gln Trp Asn Lys Pro Ser Lys Pro Lys Thr Asn
65                  70                  75                  80

Leu Lys His Val Ala Gly Ala Ala Ala Gly Ala Val Val Gly Gly
                85                  90                  95

Leu Gly Gly Tyr Met Leu Gly Ser Ala Met Ser Arg Pro Met Leu His
            100                 105                 110

Phe Gly Asn Asp Trp Glu Asp Arg Tyr Tyr Arg Glu Asn Met Tyr Arg
            115                 120                 125

Tyr Pro Asn Gln Val Tyr Tyr Arg Pro Val Asp Gln Tyr Ser Asn Gln
        130                 135                 140

Asn Asn Phe Val His Asp Cys Val Asn Ile Thr Ile Lys Gln His Thr
145                 150                 155                 160

Val Thr Thr Thr Thr Lys Gly Glu Asn Phe Thr Glu Thr Asp Val Lys
                165                 170                 175

Met Met Glu Arg Val Val Glu Gln Met Cys Val Thr Gln Tyr Gln Lys
            180                 185                 190

Glu Ser Gln Ala Tyr Tyr Asp Gly Arg Arg Ser Ser Ala Val Leu Phe
        195                 200                 205

Ser Ser Pro Pro Val Ile Leu Leu Ile Ser Leu Ile Phe Leu Ile Val
    210                 215                 220

Gly
225

<210> SEQ ID NO 8
<211> LENGTH: 256
<212> TYPE: PRT
<213> ORGANISM: Sheep

<400> SEQUENCE: 8

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gln Pro His
65                  70                  75                  80

Gly Gly Gly Trp Gly Gln Pro His Gly Gly Gly Trp Gly Gln Gly
                85                  90                  95

Gly Ser His Ser Gln Trp Asn Lys Pro Ser Lys Pro Lys Thr Asn Met
            100                 105                 110

Lys His Val Ala Gly Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Arg Tyr Ser Asn Gln Asn
                165                 170                 175

Asn Phe Val His Asp Cys Val Asn Ile Thr Val Lys Gln His Thr Val
            180                 185                 190

-continued

```
Thr Thr Thr Thr Lys Gly Glu Asn Phe Thr Glu Thr Asp Ile Lys Ile
            195                 200                 205

Met Glu Arg Val Val Glu Gln Met Cys Ile Thr Gln Tyr Gln Arg Glu
        210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 9
<211> LENGTH: 256
<212> TYPE: PRT
<213> ORGANISM: Goat

<400> SEQUENCE: 9

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Ser His Ser Asp Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly His Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser His Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Pro
225                 230                 235                 240

Pro Pro Val Ile Leu Leu Ile Ser Leu Leu Ile Leu Leu Ile Val Gly
                245                 250                 255

<210> SEQ ID NO 10
<211> LENGTH: 254
<212> TYPE: PRT
<213> ORGANISM: Syrian hamster

<400> SEQUENCE: 10

Met Ala Asn Leu Ser Tyr Trp Leu Leu Ala Leu Phe Val Ala Met Trp
1               5                   10                  15
```

```
Thr Asp Val Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
         35                  40                  45

Tyr Pro Pro Gln Gly Gly Thr Trp Gly Gln Pro His Gly Gly Gly
 50                  55                  60

Trp Gly Gln Pro His Gly Gly Trp Gly Gln Pro His Gly Gly
 65                  70                  75                  80

Trp Gly Gln Pro His Gly Gly Trp Gly Gln Gly Gly Thr His
                     85                  90                  95

Asn Gln Trp Asn Lys Pro Ser Lys Pro Lys Thr Asn Met Lys His Met
                 100                 105                 110

Ala Gly Ala Ala Ala Gly Ala Val Val Gly Gly Leu Gly Gly Tyr
             115                 120                 125

Met Leu Gly Ser Ala Met Ser Arg Pro Met Met His Phe Gly Asn Asp
     130                 135                 140

Trp Glu Asp Arg Tyr Tyr Arg Glu Asn Met Asn Arg Tyr Pro Asn Gln
145                 150                 155                 160

Val Tyr Tyr Arg Pro Val Asp Gln Tyr Asn Asn Gln Asn Asn Phe Val
                 165                 170                 175

His Asp Cys Val Asn Ile Thr Ile Lys Gln His Thr Val Thr Thr Tyr
             180                 185                 190

Thr Lys Gly Glu Asn Phe Thr Glu Thr Asp Ile Lys Ile Met Glu Arg
         195                 200                 205

Val Val Glu Gln Met Cys Thr Thr Gln Tyr Gln Lys Glu Ser Gln Ala
     210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Met Val Gly
                 245                 250

<210> SEQ ID NO 11
<211> LENGTH: 258
<212> TYPE: PRT
<213> ORGANISM: Mink

<400> SEQUENCE: 11

Met Val Lys Ser His Ile Gly Ser Trp Leu Leu Val Leu Phe Val Ala
1               5                   10                  15

Thr Trp Ser Asp Ile Gly Phe Cys Lys Lys Arg Pro Lys Pro Gly Gly
             20                  25                  30

Gly Trp Asn Thr Gly Gly Ser Arg Tyr Pro Gly Gln Gly Ser Pro Gly
         35                  40                  45

Gly Asn Arg Tyr Pro Pro Gln Gly Gly Gly Trp Gly Gln Pro His
 50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Gly Trp Gly Gln Gly
                     85                  90                  95

Gly Gly Ser His Gly Gln Trp Gly Lys Pro Ser Lys Pro Lys Thr Asn
                 100                 105                 110

Met Lys His Val Ala Gly Ala Ala Ala Gly Ala Val Val Gly Gly
             115                 120                 125

Leu Gly Gly Tyr Met Leu Gly Ser Ala Met Ser Arg Pro Leu Ile His
     130                 135                 140
```

```
Phe Gly Asn Asp Tyr Glu Asp Arg Tyr Tyr Arg Glu Asn Met Tyr Arg
145                 150                 155                 160

Tyr Pro Asn Gln Val Tyr Tyr Lys Pro Val Asp Gln Tyr Ser Asn Gln
                165                 170                 175

Asn Asn Phe Val His Asp Cys Val Asn Ile Thr Val Lys Gln His Thr
            180                 185                 190

Val Thr Thr Thr Thr Lys Gly Glu Asn Phe Thr Glu Thr Asp Met Lys
        195                 200                 205

Ile Met Glu Arg Val Val Glu Gln Met Cys Val Thr Gln Tyr Gln Arg
        210                 215                 220

Glu Ser Glu Ala Ala Tyr Tyr Gln Arg Gly Ala Ser Ala Ile Leu Phe
225                 230                 235                 240

Ser Pro Pro Val Ile Leu Leu Ile Ser Leu Leu Ile Leu Leu Ile
                245                 250                 255

Val Gly

<210> SEQ ID NO 12
<211> LENGTH: 253
<212> TYPE: PRT
<213> ORGANISM: Gorilla

<400> SEQUENCE: 12

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```

-continued

```
<210> SEQ ID NO 13
<211> LENGTH: 254
<212> TYPE: PRT
<213> ORGANISM: Chimpanzee

<400> SEQUENCE: 13

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
                100                 105                 110

Ala Gly Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Gln Tyr Ser Ser Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Leu Ile Val Gly
                245                 250

<210> SEQ ID NO 14
<211> LENGTH: 263
<212> TYPE: PRT
<213> ORGANISM: Greater Kudu

<400> SEQUENCE: 14

Met Val Lys Ser His Ile Gly Ser Trp Ile Leu Val Leu Phe Val Ala
1               5                   10                  15

Met Trp Ser Asp Val Ala Leu Cys Lys Lys Arg Pro Lys Pro Gly Gly
                20                  25                  30

Gly Trp Asn Thr Gly Gly Ser Arg Tyr Pro Gly Gln Gly Ser Pro Gly
            35                  40                  45

Gly Asn Arg Tyr Pro Ser Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
                85                  90                  95
```

```
Gly Gly Gly Gly Trp Gly Gln Gly Gly Thr His Gly Gln Trp Asn Lys
            100                 105                 110

Pro Ser Lys Lys Thr Asn Met Lys His Val Ala Gly Ala Ala Ala Ala
        115                 120                 125

Gly Ala Val Val Gly Gly Leu Gly Gly Tyr Met Leu Gly Ser Ala Met
130                 135                 140

Ser Arg Pro Leu Ile His Phe Gly Ser Asp Tyr Glu Asp Arg Tyr Tyr
145                 150                 155                 160

Arg Glu Asn Met Tyr Arg Tyr Pro Asn Gln Val Tyr Tyr Arg Pro Val
                165                 170                 175

Asp Gln Tyr Ser Asn Gln Asn Asn Phe Val His Asp Val Asn Asn Ile
                180                 185                 190

Thr Val Lys Gln His Thr Val Thr Thr Thr Lys Gly Glu Asn Phe
        195                 200                 205

Thr Glu Thr Asp Ile Lys Met Met Glu Arg Val Val Glu Gln Met Cys
210                 215                 220

Ile Thr Gln Tyr Gln Arg Glu Ser Glu Ala Tyr Tyr Gln Arg Gly Ala
225                 230                 235                 240

Ser Val Ile Leu Phe Ser Ser Pro Val Ile Leu Leu Ile Ser Phe
                245                 250                 255

Leu Ile Phe Leu Ile Val Gly
            260

<210> SEQ ID NO 15
<211> LENGTH: 255
<212> TYPE: PRT
<213> ORGANISM: Camel

<400> SEQUENCE: 15

Met Val Lys Ser His Met Gly Ser Trp Ile Leu Val Leu Phe Val Val
1               5                   10                  15

Thr Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Tyr Arg Tyr Pro Pro Gln Gly Gly Gly Trp Gly Gln Pro His
50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Trp Gly Gln Gly Gly
                85                  90                  95

Gly Ala His Gly Gln Trp Asn Lys Pro Ser Lys Pro Lys Thr Ser Met
            100                 105                 110

Lys His Val Ala Gly Ala Ala Ala Gly Ala Val Val Gly Gly Leu
        115                 120                 125

Gly Gly Tyr Met Leu Gly Ser Ala Met Ser Arg Pro Leu Ile His Phe
130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Lys Pro Val Asp Gln Tyr Ser Asn Gln Asn
                165                 170                 175

Ser Phe Val His Asp Cys Val Asn Ile Thr Val Lys Gln His Thr Val
                180                 185                 190

Thr Thr Thr Thr Lys Gly Glu Asn Phe Thr Glu Thr Asp Val Lys Met
            195                 200                 205
```

```
Met Glu Arg Val Val Glu Gln Met Cys Ile Thr Gln Tyr Gln Arg Glu
    210                 215                 220

Tyr Gln Ala Ser Tyr Arg Gly Ala Ser Val Ile Phe Ser Ser Pro
225                 230                 235                 240

Pro Val Ile Leu Leu Ile Ser Phe Leu Ile Phe Leu Ile Val Gly
                245                 250                 255

<210> SEQ ID NO 16
<211> LENGTH: 257
<212> TYPE: PRT
<213> ORGANISM: Pig

<400> SEQUENCE: 16

Met Val Lys Ser His Ile Gly Gly Trp Ile Leu Val Leu Phe Val Ala
1               5                   10                  15

Ala Trp Ser Asp Ile Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Gly Trp Gly Gln Gly
                85                  90                  95

Gly Gly Ser His Gly Gln Trp Asn Lys Pro Ser Lys Pro Lys Thr Asn
            100                 105                 110

Met Lys His Val Ala Gly Ala Ala Ala Ala Gly Ala Val Val Gly Gly
        115                 120                 125

Leu Gly Gly Tyr Met Leu Gly Ser Ala Met Ser Arg Pro Leu Ile His
    130                 135                 140

Phe Gly Ser Asp Tyr Glu Asp Arg Tyr Tyr Arg Glu Asn Met His Arg
145                 150                 155                 160

Tyr Pro Asn Gln Val Tyr Tyr Arg Pro Val Asp Gln Tyr Ser Asn Gln
                165                 170                 175

Asn Ser Phe Val His Asp Cys Val Asn Ile Thr Val Lys Glu His Thr
            180                 185                 190

Val Thr Thr Thr Thr Lys Gly Glu Asn Phe Thr Glu Thr Asp Val Lys
        195                 200                 205

Met Ile Glu Arg Val Val Glu Gln Met Cys Ile Thr Gln Tyr Gln Lys
    210                 215                 220

Glu Tyr Glu Ala Tyr Ala Gln Arg Gly Ala Ser Val Ile Leu Phe Ser
225                 230                 235                 240

Ser Pro Pro Val Ile Leu Leu Ile Ser Phe Leu Leu Phe Leu Ile Val
                245                 250                 255

Gly

<210> SEQ ID NO 17
<211> LENGTH: 253
<212> TYPE: PRT
<213> ORGANISM: Artificial
<220> FEATURE:
<223> OTHER INFORMATION: homolog of full-length human prion
<220> FEATURE:
<221> NAME/KEY: MISC_FEATURE
<222> LOCATION: (1)..(253)
<223> OTHER INFORMATION: Xaa is is Val, Val, Tyr, Met, Leu, Pro, Asp,
      Glu, Lys, Gly or Ser
```

```
<400> SEQUENCE: 17

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
                100                 105                 110

Ala Gly Ala Ala Ala Ala Gly Ala Xaa Xaa Xaa Gly Gly Leu Gly Gly
            115                 120                 125

Xaa Xaa Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 18
<211> LENGTH: 264
<212> TYPE: PRT
<213> ORGANISM: Artificial
<220> FEATURE:
<223> OTHER INFORMATION: homolog of bovine full-length prion
<220> FEATURE:
<221> NAME/KEY: MISC_FEATURE
<222> LOCATION: (1)..(264)
<223> OTHER INFORMATION: Xaa is Val, Val, Tyr, Met, Leu, Pro, Asp, Glu,
      Lys, Gly, or Ser

<400> SEQUENCE: 18

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80
```

-continued

```
Gly Gly Gly Trp Gly Gln Pro His Gly Gly Trp Gly Gln Pro His
                85                  90                  95
Gly Gly Gly Gly Trp Gly Gln Gly Thr His Gly Gln Trp Asn Lys
            100                 105                 110
Pro Ser Lys Pro Lys Thr Asn Met Lys His Val Ala Gly Ala Ala
            115                 120                 125
Ala Gly Ala Xaa Xaa Gly Gly Leu Gly Gly Xaa Xaa Xaa Gly Ser Ala
            130                 135                 140
Met Ser Arg Pro Leu Ile His Phe Gly Ser Asp Tyr Glu Asp Arg Tyr
145                 150                 155                 160
Tyr Arg Glu Asn Met His Arg Tyr Pro Asn Gln Val Tyr Tyr Arg Pro
                165                 170                 175
Val Asp Gln Tyr Ser Asn Gln Asn Asn Phe Val His Asp Cys Val Asn
                180                 185                 190
Ile Thr Val Lys Glu His Thr Val Thr Thr Thr Thr Lys Gly Glu Asn
                195                 200                 205
Phe Thr Glu Thr Asp Ile Lys Met Met Glu Arg Val Val Glu Gln Met
                210                 215                 220
Cys Ile Thr Gln Tyr Gln Arg Glu Ser Gln Ala Tyr Tyr Gln Arg Gly
225                 230                 235                 240
Ala Ser Val Ile Leu Phe Ser Ser Pro Pro Val Ile Leu Leu Ile Ser
                245                 250                 255
Phe Leu Ile Phe Leu Ile Val Gly
                260

<210> SEQ ID NO 19
<211> LENGTH: 65
<212> TYPE: PRT
<213> ORGANISM: Artificial
<220> FEATURE:
<223> OTHER INFORMATION: homolog of fragment of human prion
<220> FEATURE:
<221> NAME/KEY: MISC_FEATURE
<222> LOCATION: (1)..(10)
<223> OTHER INFORMATION: Xaa is an optional poly-Lys or poly-Asp segment
      of 4-10 residues
<220> FEATURE:
<221> NAME/KEY: MISC_FEATURE
<222> LOCATION: (42)..(51)
<223> OTHER INFORMATION: Xaa is Val, Val, Tyr, Met, Leu, Pro, Asp, Glu,
      Lys, Gly, or Ser

<400> SEQUENCE: 19

Xaa Xaa Xaa Xaa Xaa Xaa Xaa Xaa Xaa Xaa Gly Gln Gly Gly Gly Thr
1               5                   10                  15
His Ser Gln Trp Asn Lys Pro Ser Lys Pro Lys Thr Asn Met Lys His
                20                  25                  30
Met Ala Gly Ala Ala Ala Ala Gly Ala Xaa Xaa Gly Gly Leu Gly Gly
            35                  40                  45
Xaa Xaa Xaa Gly Ser Ala Met Ser Arg Pro Ile Ile His Phe Gly Ser
        50                  55                  60
Asp
65

<210> SEQ ID NO 20
<211> LENGTH: 120
<212> TYPE: PRT
<213> ORGANISM: Artificial
<220> FEATURE:
<223> OTHER INFORMATION: homolog of fragment of human prion
<220> FEATURE:
```

```
<221> NAME/KEY: MISC_FEATURE
<222> LOCATION: (1)..(10)
<223> OTHER INFORMATION: Xaa is an optional poly-Lys or poly-Asp segment
      of 4-10 residues
<220> FEATURE:
<221> NAME/KEY: MISC_FEATURE
<222> LOCATION: (42)..(106)
<223> OTHER INFORMATION: Xaa is Val, Val, Tyr, Met, Leu, Pro, Asp, Glu,
      Lys, Gly, or Ser

<400> SEQUENCE: 20

Xaa Xaa Xaa Xaa Xaa Xaa Xaa Xaa Xaa Xaa Gly Gln Gly Gly Gly Thr
1               5                   10                  15

His Ser Gln Trp Asn Lys Pro Ser Lys Pro Lys Thr Asn Met Lys His
            20                  25                  30

Met Ala Gly Ala Ala Ala Ala Gly Ala Xaa Xaa Gly Gly Leu Gly Gly
        35                  40                  45

Xaa Xaa Xaa Gly Ser Ala Met Ser Arg Pro Ile Ile His Phe Gly Ser
    50                  55                  60

Asp Gly Gln Gly Gly Gly Thr His Ser Gln Trp Asn Lys Pro Ser Lys
65                  70                  75                  80

Pro Lys Thr Asn Met Lys His Met Ala Gly Ala Ala Ala Ala Gly Ala
                85                  90                  95

Xaa Xaa Gly Gly Leu Gly Gly Xaa Xaa Xaa Gly Ser Ala Met Ser Arg
            100                 105                 110

Pro Ile Ile His Phe Gly Ser Asp
            115                 120

<210> SEQ ID NO 21
<211> LENGTH: 65
<212> TYPE: PRT
<213> ORGANISM: Artificial
<220> FEATURE:
<223> OTHER INFORMATION: homolog of fragment of human prion
<220> FEATURE:
<221> NAME/KEY: MISC_FEATURE
<222> LOCATION: (32)..(41)
<223> OTHER INFORMATION: Xaa is Val, Tyr, Met, Leu, Pro, Asp, Glu, Lys,
      Gly, or Ser
<220> FEATURE:
<221> NAME/KEY: MISC_FEATURE
<222> LOCATION: (56)..(65)
<223> OTHER INFORMATION: Xaa is an optional poly-Lys or poly-Asp segment
      of 4-10 residues

<400> SEQUENCE: 21

Gly Gln Gly Gly Gly Thr His Ser Gln Trp Asn Lys Pro Ser Lys Pro
1               5                   10                  15

Lys Thr Asn Met Lys His Met Ala Gly Ala Ala Ala Ala Gly Ala Xaa
            20                  25                  30

Xaa Gly Gly Leu Gly Gly Xaa Xaa Xaa Gly Ser Ala Met Ser Arg Pro
        35                  40                  45

Ile Ile His Phe Gly Ser Asp Xaa Xaa Xaa Xaa Xaa Xaa Xaa Xaa
    50                  55                  60

Xaa
65

<210> SEQ ID NO 22
<211> LENGTH: 120
<212> TYPE: PRT
<213> ORGANISM: Artificial
<220> FEATURE:
<223> OTHER INFORMATION: homolog of fragment of human prion
<220> FEATURE:
<221> NAME/KEY: MISC_FEATURE
```

```
<222> LOCATION: (32)..(96)
<223> OTHER INFORMATION: Xaa is Val, Tyr, Met, Leu, Pro, Asp, Glu, Lys,
      Gly, or Ser
<220> FEATURE:
<221> NAME/KEY: MISC_FEATURE
<222> LOCATION: (111)..(120)
<223> OTHER INFORMATION: Xaa is an optional poly-Lys or poly-Asp segment
      of 4-10 residues

<400> SEQUENCE: 22

Gly Gln Gly Gly Gly Thr His Ser Gln Trp Asn Lys Pro Ser Lys Pro
1               5                   10                  15

Lys Thr Asn Met Lys His Met Ala Gly Ala Ala Ala Gly Ala Xaa
            20                  25                  30

Xaa Gly Gly Leu Gly Gly Xaa Xaa Xaa Gly Ser Ala Met Ser Arg Pro
            35                  40                  45

Ile Ile His Phe Gly Ser Asp Gly Gln Gly Gly Thr His Ser Gln
    50                  55                  60

Trp Asn Lys Pro Ser Lys Pro Lys Thr Asn Met Lys His Met Ala Gly
65                  70                  75                  80

Ala Ala Ala Ala Gly Ala Xaa Xaa Gly Gly Leu Gly Gly Xaa Xaa Xaa
                85                  90                  95

Gly Ser Ala Met Ser Arg Pro Ile Ile His Phe Gly Ser Asp Xaa Xaa
            100                 105                 110

Xaa Xaa Xaa Xaa Xaa Xaa Xaa Xaa
            115                 120

<210> SEQ ID NO 23
<211> LENGTH: 75
<212> TYPE: PRT
<213> ORGANISM: Artificial
<220> FEATURE:
<223> OTHER INFORMATION: homolog of fragment of human prion
<220> FEATURE:
<221> NAME/KEY: MISC_FEATURE
<222> LOCATION: (1)..(10)
<223> OTHER INFORMATION: Xaa is an optional poly-Lys or poly-Asp segment
      of 4-10 residues
<220> FEATURE:
<221> NAME/KEY: MISC_FEATURE
<222> LOCATION: (42)..(51)
<223> OTHER INFORMATION: Xaa is Val, Tyr, Met, Leu, Pro, Asp, Glu, Lys,
      Gly, or Ser
<220> FEATURE:
<221> NAME/KEY: MISC_FEATURE
<222> LOCATION: (66)..(75)
<223> OTHER INFORMATION: Xaa is an optional poly-Lys or poly-Asp segment
      of 4-10 residues

<400> SEQUENCE: 23

Xaa Xaa Xaa Xaa Xaa Xaa Xaa Xaa Xaa Xaa Gly Gln Gly Gly Gly Thr
1               5                   10                  15

His Ser Gln Trp Asn Lys Pro Ser Lys Pro Lys Thr Asn Met Lys His
            20                  25                  30

Met Ala Gly Ala Ala Ala Ala Gly Ala Xaa Xaa Gly Gly Leu Gly Gly
            35                  40                  45

Xaa Xaa Xaa Gly Ser Ala Met Ser Arg Pro Ile Ile His Phe Gly Ser
    50                  55                  60

Asp Xaa Xaa Xaa Xaa Xaa Xaa Xaa Xaa Xaa Xaa
65                  70                  75

<210> SEQ ID NO 24
<211> LENGTH: 130
<212> TYPE: PRT
<213> ORGANISM: Artificial
```

```
<220> FEATURE:
<223> OTHER INFORMATION: homolog of fragment of human prion
<220> FEATURE:
<221> NAME/KEY: MISC_FEATURE
<222> LOCATION: (1)..(10)
<223> OTHER INFORMATION: Xaa is an optional poly-Lys or poly-Asp segment
      of 4-10 residues
<220> FEATURE:
<221> NAME/KEY: MISC_FEATURE
<222> LOCATION: (42)..(106)
<223> OTHER INFORMATION: Xaa is Val, Tyr, Met, Leu, Pro, Asp, Glu, Lys,
      Gly, or Ser
<220> FEATURE:
<221> NAME/KEY: MISC_FEATURE
<222> LOCATION: (121)..(130)
<223> OTHER INFORMATION: Xaa is an optional poly-Lys or poly-Asp segment
      of 4-10 residues

<400> SEQUENCE: 24

Xaa Xaa Xaa Xaa Xaa Xaa Xaa Xaa Xaa Gly Gln Gly Gly Gly Thr
 1               5                  10                  15

His Ser Gln Trp Asn Lys Pro Ser Lys Pro Lys Thr Asn Met Lys His
            20                  25                  30

Met Ala Gly Ala Ala Ala Ala Gly Ala Xaa Xaa Gly Gly Leu Gly Gly
            35                  40                  45

Xaa Xaa Xaa Gly Ser Ala Met Ser Arg Pro Ile Ile His Phe Gly Ser
50                  55                  60

Asp Gly Gln Gly Gly Gly Thr His Ser Gln Trp Asn Lys Pro Ser Lys
65                  70                  75                  80

Pro Lys Thr Asn Met Lys His Met Ala Gly Ala Ala Ala Ala Gly Ala
            85                  90                  95

Xaa Xaa Gly Gly Leu Gly Gly Xaa Xaa Xaa Gly Ser Ala Met Ser Arg
        100                 105                 110

Pro Ile Ile His Phe Gly Ser Asp Xaa Xaa Xaa Xaa Xaa Xaa Xaa
            115                 120                 125

Xaa Xaa
    130

<210> SEQ ID NO 25
<211> LENGTH: 73
<212> TYPE: PRT
<213> ORGANISM: Artificial
<220> FEATURE:
<223> OTHER INFORMATION: homolog of fragment of bovine prion
<220> FEATURE:
<221> NAME/KEY: MISC_FEATURE
<222> LOCATION: (1)..(10)
<223> OTHER INFORMATION: Xaa is an optional poly-Lys or poly-Asp segment
      of 4-10 residues
<220> FEATURE:
<221> NAME/KEY: MISC_FEATURE
<222> LOCATION: (50)..(59)
<223> OTHER INFORMATION: Xaa is Val, Val, Tyr, Met, Leu, Pro, Asp, Glu,
      Lys, Gly, or Ser

<400> SEQUENCE: 25

Xaa Xaa Xaa Xaa Xaa Xaa Xaa Xaa Xaa Xaa Gly Gln Pro His Gly Gly
 1               5                  10                  15

Gly Gly Trp Gly Gln Gly Gly Thr His Gly Gln Trp Asn Lys Pro Ser
            20                  25                  30

Lys Pro Lys Thr Asn Met Lys His Val Ala Gly Ala Ala Ala Ala Gly
            35                  40                  45

Ala Xaa Xaa Gly Gly Leu Gly Gly Xaa Xaa Xaa Gly Ser Ala Met Ser
50                  55                  60

Arg Pro Leu Ile His Phe Gly Asn Asp
```

65          70

<210> SEQ ID NO 26
<211> LENGTH: 136
<212> TYPE: PRT
<213> ORGANISM: Artificial
<220> FEATURE:
<223> OTHER INFORMATION: homolog of fragment of bovine prion
<220> FEATURE:
<221> NAME/KEY: MISC_FEATURE
<222> LOCATION: (1)..(10)
<223> OTHER INFORM Xaa Xaa Xaa Xaa Xaa Xaa Xaa Xaa Xaa
65                  70

<210> SEQ ID NO 28
<211> LENGTH: 136
<212> TYPE: PRT
<213> ORGANISM: Artificial
<220> FEATURE:
<223> OTHER INFORMATION: homolog of fragment of bovine prion
<220> FEATURE:
<221> NAME/KEY: MISC_FEATURE
<222> LOCATION: (40)..(112)
<223> OTHER INFORMATION: Xaa is Val, Val, Tyr, Met, Leu, Pro, Asp, Glu, Lys, Gly, or Ser
<220> FEATURE:
<221> NAME/KEY: MISC_FEATURE
<222> LOCATION: (127)..(136)
<223> OTHER INFORMATION: Xaa is an optional poly-Lys or poly-Asp segment of 4-10 residues

<400> SEQUENCE: 28

Gly Gln Pro His Gly Gly Gly Gly Trp Gly Gln Gly Gly Thr His Gly
1 5 10 15

Gln Trp Asn Lys Pro Ser Lys Pro Lys Thr Asn Met Lys His Val Ala
20 25 30

Gly Ala Ala Ala Ala Gly Ala Xaa Xaa Gly Gly Leu Gly Gly Xaa Xaa
35 40 45

Xaa Gly Ser Ala Met Ser Arg Pro Leu Ile His Phe Gly Asn Asp Gly
50 55 60

Gln Pro His Gly Gly Gly Gly Trp Gly Gln Gly Gly Thr His Gly Gln
65 70 75 80

Trp Asn Lys Pro Ser Lys Pro Lys Thr Asn Met Lys His Val Ala Gly
85 90 95

Ala Ala Ala Ala Gly Ala Xaa Xaa Gly Gly Leu Gly Gly Xaa Xaa Xaa
100 105 110

Gly Ser Ala Met Ser Arg Pro Leu Ile His Phe Gly Asn Asp Xaa Xaa
115 120 125

Xaa Xaa Xaa Xaa Xaa Xaa Xaa Xaa
130 135

<210> SEQ ID NO 29
<211> LENGTH: 83
<212> TYPE: PRT
<213> ORGANISM: Artificial
<220> FEATURE:
<223> OTHER INFORMATION: homolog of fragment of bovine prion
<220> FEATURE:
<221> NAME/KEY: MISC_FEATURE
<222> LOCATION: (1)..(10)
<223> OTHER INFORMATION: Xaa is an optional poly-Lys or poly-Asp segment of 4-10 residues
<220> FEATURE:
<221> NAME/KEY: MISC_FEATURE
<222> LOCATION: (50)..(59)
<223> OTHER INFORMATION: Xaa is Val, Val, Tyr, Met, Leu, Pro, Asp, Glu, Ly, Gly, or Ser
<220> FEATURE:
<221> NAME/KEY: MISC_FEATURE
<222> LOCATION: (74)..(83)
<223> OTHER INFORMATION: Xaa is an optional poly-Lys or poly-Asp segment of 4-10 residues

<400> SEQUENCE: 29

Xaa Xaa Xaa Xaa Xaa Xaa Xaa Xaa Xaa Xaa Gly Gln Pro His Gly Gly
1 5 10 15

Gly Gly Trp Gly Gln Gly Gly Thr His Gly Gln Trp Asn Lys Pro Ser

```
                       20                  25                  30
Lys Pro Lys Thr Asn Met Lys His Val Ala Gly Ala Ala Ala Gly
             35                  40                  45

Ala Xaa Xaa Gly Gly Leu Gly Gly Xaa Xaa Xaa Gly Ser Ala Met Ser
     50                  55                  60

Arg Pro Leu Ile His Phe Gly Asn Asp Xaa Xaa Xaa Xaa Xaa Xaa
 65                  70                  75                  80

Xaa Xaa Xaa

<210> SEQ ID NO 30
<211> LENGTH: 136
<212> TYPE: PRT
<213> ORGANISM: Artificial
<220> FEATURE:
<223> OTHER INFORMATION: homolog of fragment of bovine prion
<220> FEATURE:
<221> NAME/KEY: MISC_FEATURE
<222> LOCATION: (1)..(10)
<223> OTHER INFORMATION: Xaa is an optional poly-Lys or poly-Asp segment
      of 4-10 residues
<220> FEATURE:
<221> NAME/KEY: MISC_FEATURE
<222> LOCATION: (50)..(122)
<223> OTHER INFORMATION: Xaa is Val, Val, Tyr, Met, Leu, Pro, Asp, Glu,
      Lys, Gly, or Ser
<220> FEATURE:
<221> NAME/KEY: MISC_FEATURE
<222> LOCATION: (127)..(136)
<223> OTHER INFORMATION: Xaa is an optional poly-Lys or poly-Asp segment
      of 4-10 residues

<400> SEQUENCE: 30

Xaa Xaa Xaa Xaa Xaa Xaa Xaa Xaa Xaa Xaa Gly Gln Pro His Gly Gly
 1               5                  10                  15

Gly Gly Trp Gly Gln Gly Gly Thr His Gly Gln Trp Asn Lys Pro Ser
             20                  25                  30

Lys Pro Lys Thr Asn Met Lys His Val Ala

```
                    35                  40                  45
Asn Ile Pro Gln Arg Asp Gly Gly Thr His Leu Ala Gly Phe Arg Gly
    50                  55                  60

Ala Leu Thr Arg Thr Leu Asn Asn Tyr Met Asp Lys Glu Gly Phe Ser
65                  70                  75                  80

Lys Lys Ala Gln Ala Ala Thr Ser Gly Asp Asp Ala Arg Glu Gly Leu
                85                  90                  95

Thr Ala Val Val Ser Val Lys Val Pro Asp Pro Lys Phe Ser Ser Gln
            100                 105                 110

Thr Lys Asp Lys Leu Val Ser Ser Glu Val Lys Ser Ala Val Glu Ser
            115                 120                 125

Ala Met Asn Glu Lys Leu Ala Asp Phe Leu Ala Glu Asn Pro Ser Glu
        130                 135                 140

Ala Lys Asn Val Cys Ser Lys Ile Ile Asp Ala Ala Arg Ala Arg Glu
145                 150                 155                 160

Ala Ala Arg Lys Ala Arg Glu Met Thr Arg Arg Lys Gly Ala Leu Asp
                165                 170                 175

Leu Ala Gly Leu Pro Gly Lys Leu Ala Asp Cys Gln Glu Lys Asp Pro
            180                 185                 190

Ala Leu Ser Glu Leu Tyr Ile
            195

<210> SEQ ID NO 32
<211> LENGTH: 10
<212> TYPE: PRT
<213> ORGANISM: Artificial
<220> FEATURE:
<223> OTHER INFORMATION: homolog of fragment of human or bovine prion
<220> FEATURE:
<221> NAME/KEY: MISC_FEATURE
<222> LOCATION: (1)..(10)
<223> OTHER INFORMATION: Xaa is Val, Val, Tyr, Met, Leu, Pro, Asp, Glu,
      Lys, Gly, or Ser

<400> SEQUENCE: 32

Xaa Xaa Gly Gly Leu Gly Gly Xaa Xaa Xaa
1               5                   10
```

The invention claimed is:

1. An immunogenic composition comprising an attenuated bacterium microorganism consisting of one of a *Shigella* strain and a *Salmonella* strain transformed with a vector expressing a non-infectious, non-pathogenic mammalian prion protein selected from the group consisting of mouse, bovine, deer, elk, and sheep prion protein, wherein the composition is suitable for mucosal administration.

2. The composition of claim 1, wherein the prion protein comprises a fragment of a prion protein which consists of residues 93-156 of one of SEQ ID NO:2, SEQ ID NO:3, SEQ ID NO:4, and SEQ ID NO:8.

3. A method of preventing or treating a prion disease in a mammalian subject in need thereof, comprising mucosally administering to said subject the immunogenic composition of claim 1.

4. The method of claim 3, wherein the mammalian subject is selected from the group consisting of bovine, deer, elk, and sheep.

5. The method of claim 3, wherein the mucosal administration is selected from the group consisting of oral, intragastric, intranasal, rectal and intraocular administration.

6. The method of claim 3, wherein the subject is bovine and the prion disease is bovine spongiform encephalopathy.

7. The method of claim 3, wherein the subject is deer or elk and the prion disease is chronic wasting disease.

8. The method of claim 3, wherein the subject is sheep and the prion disease is scrapie.

9. The method of claim 3, further comprising repeating the mucosal administration at least once.

10. The method of claim 9, comprising repeating the mucosal administration within one month after the first administration.

11. The composition of claim 1, wherein the prion protein comprises a fragment of a prion protein which consists of residues 123-225 of one of SEQ ID NO:2, SEQ ID NO:3, SEQ ID NO:4, and SEQ ID NO:8.

12. The composition of claim 1, wherein the attenuated bacterium microorganism is a *Salmonella* strain.

13. The composition of claim 12, wherein the *Salmonella* strain is selected from the group consisting of *Salmonella typhimurium* LVR01 and SL3261, and *Salmonella typhi* Ty21a.

14. The composition of claim 1, wherein the attenuated bacterium microorganism is a *Shigella* strain.

15. The composition of claim 1, further comprising aluminum hydroxide.

* * * * *

UNITED STATES PATENT AND TRADEMARK OFFICE
CERTIFICATE OF CORRECTION

| | | |
|---|---|---|
| PATENT NO. | : 8,685,718 B2 | |
| APPLICATION NO. | : 10/558276 | |
| DATED | : April 1, 2014 | |
| INVENTOR(S) | : Wisniewski et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 609 days.

Signed and Sealed this
First Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,685,718 B2
APPLICATION NO. : 10/558276
DATED : April 1, 2014
INVENTOR(S) : Thomas Wisniewski et al.

Page 1 of 1

It is certified that error appears in the above-identified patent and that said Letters Patent is hereby corrected as shown below:

In the Specification

At Column 1, in Line 13, add the following paragraphs:

--STATEMENT REGARDING FEDERALLY SPONSORED RESEARCH
This invention was made with government support under Grant Nos. R01NS47433, R03TW006848, R21AG028187-01A1, R01AR02594, ARRANS047433-06S1, and R01AG020197 awarded by the National Institutes of Health. The government has certain rights in the invention.

SEQUENCE LISTING
The instant application contains a Sequence Listing which has been submitted in ASCII format via EFS-Web and is hereby incorporated by reference in its entirety. Said ASCII copy, is named US14174717.txt, and is approximately 59,263 bytes in size.--

Signed and Sealed this
Twentieth Day of June, 2017

Joseph Matal
*Performing the Functions and Duties of the
Under Secretary of Commerce for Intellectual Property and
Director of the United States Patent and Trademark Office*